(12) United States Patent
Göbel

(10) Patent No.: US 11,207,507 B2
(45) Date of Patent: *Dec. 28, 2021

(54) DEVICE FOR THE TRANS-ANAL DRAINAGE OF STOOL FROM THE RECTUM OF A PATIENT AND/OR FOR THE TRANS-ANAL APPLICATION OF INFLOWING LIQUID THROUGH A CATHETER-LIKE ELEMENT

(71) Applicant: Advanced Medical Balloons GmbH, Waghäusel (DE)

(72) Inventor: Fred Göbel, Speyer (DE)

(73) Assignee: Advanced Medical Balloons GmbH, Waghäusel (DE)

( * ) Notice: Subject to any disclaimer, the term of this patent is extended or adjusted under 35 U.S.C. 154(b) by 99 days.

This patent is subject to a terminal disclaimer.

(21) Appl. No.: 16/276,956

(22) Filed: Feb. 15, 2019

(65) Prior Publication Data
US 2019/0275305 A1  Sep. 12, 2019

Related U.S. Application Data

(63) Continuation-in-part of application No. 14/239,971, filed as application No. PCT/EP2012/003534 on Aug. 20, 2012, now Pat. No. 10,238,842.

(30) Foreign Application Priority Data

Aug. 20, 2011 (DE) .................. 10 2011 111 225.5
Nov. 21, 2011 (DE) .................. 10 2011 118 943.6
(Continued)

(51) Int. Cl.
*A61M 25/10* (2013.01)
*A61M 27/00* (2006.01)
*A61F 5/00* (2006.01)

(52) U.S. Cl.
CPC ............ *A61M 27/00* (2013.01); *A61F 5/0093* (2013.01); *A61M 25/1002* (2013.01);
(Continued)

(58) Field of Classification Search
CPC .............. A61M 27/00; A61M 25/1002; A61M 2025/1059; A61M 2202/068;
(Continued)

(56) References Cited

U.S. PATENT DOCUMENTS 4,555,242 A    11/1985  Saucagar
4,686,985 A *   8/1987  Lottick .................. A61M 29/02
                                                            604/913
(Continued)

FOREIGN PATENT DOCUMENTS

CN           1485018        3/2004
CN          103957837       7/2016
(Continued)

*Primary Examiner* — Jenna Zhang
(74) *Attorney, Agent, or Firm* — Pandiscio & Pandiscio

(57) ABSTRACT

A device for emptying stool from the rectum of a patient by means of a shaft body which is introduced into the bowel via the anus and is able to buckle or fold axially and radially, and which is provided with a dumbbell- or hourglass-shaped balloon body for assuring the transanal positioning of the device. The invention is further characterized by the special design of and choice of material for the shaft body and the balloon envelope and by the specific positioning of the balloon body on the shaft body, wherein the axial deflection of the free forward end of the shaft body is limited or an uncontrolled deflection of the shaft is prevented, and the probability of perforation of the bowel wall under the effect of force acting on the shaft body from an axial direction is therefore decisively reduced by the intestinal tube described according to the invention.

38 Claims, 10 Drawing Sheets

(30) Foreign Application Priority Data

| Dec. 16, 2011 | (DE) | ...................... | 10 2011 121 202.0 |
| Apr. 25, 2012 | (DE) | ...................... | 10 2012 008 361.0 |
| May 3, 2012 | (DE) | ...................... | 10 2012 008 663.6 |

(52) U.S. Cl.
CPC . *A61M 25/1029* (2013.01); *A61M 2025/1059* (2013.01); *A61M 2025/1084* (2013.01); *A61M 2202/068* (2013.01); *A61M 2205/0216* (2013.01); *A61M 2210/1067* (2013.01)

(58) Field of Classification Search
CPC ........... A61M 2210/01067; A61M 2205/0216; A61M 25/04; A61M 25/0052; A61M 2025/1065; A61M 2025/1084; A61M 2210/1067; A61F 5/0093

See application file for complete search history.

(56) References Cited

U.S. PATENT DOCUMENTS

| 6,024,092 | A | 2/2000 | De Matthaeis |
| 2003/0073974 | A1 | 4/2003 | Faicener |
| 2007/0021651 | A1* | 1/2007 | Gobel ..................... A61F 5/445 600/31 |
| 2007/0213661 | A1* | 9/2007 | Gobel ..................... A61F 2/0013 604/96.01 |
| 2009/0043151 | A1 | 2/2009 | Gabel |
| 2009/0149880 | A1 | 6/2009 | Gabel |
| 2010/0022976 | A1* | 1/2010 | Weig ..................... A61F 2/0027 604/355 |

FOREIGN PATENT DOCUMENTS

| DE | 10 2004 033 425 | 7/2006 | |
| EP | 1023913 | 8/2000 | |
| FR | 2 480 127 | 10/1981 | |
| JP | H03-116847 | 5/1991 | |
| JP | H10-234854 | 9/1998 | |
| JP | 6312258 | 4/2018 | |
| WO | WO 2004/101059 | 11/2004 | |
| WO | WO 2006/010556 | 2/2006 | |
| WO | WO 2007/118621 | 10/2007 | |
| WO | WO-2007118621 A1 * | 10/2007 | ........... A61F 2/0013 |
| WO | WO 2008/103788 | 8/2008 | |
| WO | WO 2011/012323 | 2/2011 | |

* cited by examiner

DEVICE FOR THE TRANS-ANAL DRAINAGE OF STOOL FROM THE RECTUM OF A PATIENT AND/OR FOR THE TRANS-ANAL APPLICATION OF INFLOWING LIQUID THROUGH A CATHETER-LIKE ELEMENT

REFERENCE TO PENDING PRIOR PATENT APPLICATIONS

This patent application is a continuation-in-part of pending prior U.S. patent application Ser. No. 14/239,971, filed 29 May 2014 by Fred Gabel for DEVICE FOR THE TRANS-ANAL DRAINAGE OF STOOL FROM THE RECTUM OF A PATIENT AND/OR FOR THE TRANS-ANAL APPLICATION OF INFLOWING LIQUID THROUGH A CATHETER-LIKE ELEMENT, which claims benefit of International (PCT) Patent Application No. PCT/EP2012/003534, filed 20 Aug. 2012 by Fred Göbel and Advanced Medical Balloons for DEVICE FOR THE TRANS-ANAL DRAINAGE OF STOOL FROM THE RECTUM OF A PATIENT AND/OR FOR THE TRANS-ANAL APPLICATION OF INFLOWING LIQUID THROUGH A CATHETER-LIKE ELEMENT, which in turn claims benefit of:
  (i) German Patent Application No. DE 102011111225.5, filed 20 Aug. 2011;
  (ii) German Patent Application No. DE 102011118943.6, filed 21 Nov. 2011;
  (iii) German Patent Application No. DE 102011121202.0, filed 16 Dec. 2011;
  (iv) German Patent Application No. DE 102012008361.0, filed 25 Apr. 2012; and
  (v) German Patent Application No. DE 102012008663.6, filed 3 May 2012.

The seven (7) above-identified patent applications are hereby incorporated herein by reference.

FIELD OF THE INVENTION

The invention relates to a device for the transanal drainage of stool from the rectum of a patient and/or for the transanal administration of inflowing liquid through a catheter-like element, comprising an inflatable balloon that is produced from a thin-walled soft film material of limited elastic deformability and is preformed during production with a waisted dumbbell shape or a mushroom shape.

The waisted balloon shape is formed by two terminal balloon sections with a larger tubular radius and, disposed therebetween and tapered relative thereto, a middle balloon section that has a reduced tubular radius and is placed transanally. Upon use, the distally adjoining radially enlarged balloon section is placed intrarectally, and the proximally adjoining radially enlarged balloon section is placed extracorporeally, while the tapered middle section is placed transanally.

The mushroom shaped balloon comprises one terminal balloon section with a larger tubular radius for intrarectal placement as well as a proximally adjoining tapered balloon section for transanal positioning.

In both embodiments of the device, the preformed balloon is resting on a tube-like shaft component, granting access to the rectum and the colon of the patient. The shaft component is made from an elastically deformable and self-erecting material, allowing for a radial collapse, infolding or invagination of the tube shaft envelope inside the anal canal at normal sphincter tone, and erecting the shaft gradually to its preformed shape spontaneously, when the sphincter tone is lowered and the anus is opening. Further, the shaft component preferably allows for an axial kinking or buckling, in case the device is luxating from its regular trans-anal seal position into higher segments of the large bowel, in particular into the transition area of the rectum to the sigmoidal colon, thus preventing a perforating trauma of the bowel wall, which is known as a frequently observed complication, caused by conventional devices, typically integrating a shaft element of limited radial and axial deformability.

BACKGROUND OF THE INVENTION

Devices for the temporary transanal drainage of stool have been known in a wide variety of embodiments for many years.

The patent specification DE 102004033425 B4 describes a sealing system for the management of rectal or anal incontinence having a particular embodiment for the tamponade of bleeding hemorrhoids, in which a waisted balloon element is provided at its ends with an intrarectal and a preanal section. The balloon envelope of the device is placed on the balloon-supporting shaft body in such a way that during filling, the intrarectal balloon segment moves toward the rectal floor and exerts a tamponade pressure on the bleeding venous blood vessels there. Correspondingly, the preanal balloon segment moves toward the external anal opening. This results in a tamponade effect directed axially onto the anus from both sides. In addition to axial tamponade of the bleeding, the middle, waisted section of the balloon expands outward radially to the wall of the anal canal. It is preferably shaped with a diameter that exceeds the diameter of the open anal canal. In the described device for the acute management of venous anorectal bleeding, in the in-use state the tip of the shaft body protrudes freely and unprotectedly into the intestinal lumen and poses a considerable risk of injury when retained for a dwell time beyond that required for a procedure.

The arrangement according to WO/EP2007/118621 A1 suffers from the same disadvantages. That document also describes a dumbbell- or hourglass-shaped balloon sealing system. The object here is to provide a seal against involuntary leakage of stool for intermittent periods of a few hours in chronically anorectally incontinent patients. This managing device also prominently features the rolling movement of the terminal balloon segments from both sides axially toward the anus. Here again, in the transanally placed state, the tip of the shaft body supporting the balloon protrudes freely and potentially traumatizingly into the intestinal lumen, thus making it impossible to use the sealing body with its integrated shaft for relatively long periods without risk.

From the disadvantages of the prior art comes the problem initiating the invention: to ensure, in an arrangement of the above species, that even in the most unfavorable cases the distal end of the catheter shaft does not protrude uncontrolledly into the intestinal canal and potentially cause injuries there.

SUMMARY OF THE INVENTION

This problem is solved, in a device of the above species, by virtue of the fact that both ends of the balloon taper and are fixed in a simply invaginated state, at an axial distance from each other, on the jacket surface of the catheter shaft, wherein in a preferred embodiment, the intrarectal balloon section fully surrounds the distal region of the catheter shaft in the force-free state and is tightly dimensioned such that upon axial deflection of the catheter shaft toward the bowel, due to the resultant deformation of the balloon envelope surrounding the shaft end an oppositely acting force is generated that damps and/or limits the distal end of the catheter in its movement in a distal direction, thus preventing it from emerging, in a manner potentially traumatizing to the bowel, from the distal or intrarectal balloon enlargement surrounding the shaft end.

In contrast to the prior art, the transanally placed drainage catheters described in the context of the invention primarily address the atraumatic securing of the shaft tip inside the intrarectal balloon segment in the event of an axial deflection of the catheter shaft toward the body of the patient. Perforations of the bowel wall exposed to the free distal end of the shaft body are prevented to the greatest possible extent by the inventive implementation of the device.

In an alternative, less preferable embodiment of the above described shaft excursion damping structural transition from the distal balloon end to the distal shaft opening, the balloon carrying shaft tube component can be distally extended beyond the distal balloon radius by a tapered, cone- or olive-shaped element for facilitating the ease of anal insertion of the device. The insertion aiding element is preferably made from a soft foam or gel-based material. In case of an axially directed luxation of the device from the transanal position into higher bowel segments, perforating injuries of the bowel wall are being prevented by the above described, elastic axial buckling of the shaft tube component.

The elastic deformation and elastic erection of the balloon carrying shaft segment can be modified by foam or gel-based layers, coating the outer or inner surface of the shaft tube component. Alternative to supplementary, coating material layers, the envelope of the shaft tube component can be molded to a particular profile, as e.g. a ring- or spiral-shaped corrugation. Such an elastically reinforcing, corrugated profile of the tube envelope allows for a reduction of shaft wall thickness, while at the same time enhancing the radial collapse and axial buckling properties of the shaft tube component. The corrugated profiling of the shaft can be combined with additional elasticity modifying material layers, coating or mesh-like covering the entire length of the balloon carrying portion of the shaft tube or only segments of it.

It is a basic, important functional concept of the present invention, that the balloon carrying shaft segment of the device withstands a certain balloon filling pressure without a lumen occluding, complete radial collapse of the shaft component, and maintains its preformed cross-section opened or partially opened to an extent, that does not impair the efficient drainage of the fluid bowel content. The force that is elastically erecting the shaft tube envelope is larger than the force resting on the outside of the shaft tube, which is exerted by the filling pressure acting inside the balloon. When positioned inside the anal canal, the force which is exerted on the balloon carrying segment of the shaft tube envelope by the anal sphincter muscle, at a normal sphincter tone, shall cause a radial collapse or a radial infolding or invagination of the shaft wall. For the consistent atraumatic performance and the prevention of a functional or structural damage of the anal closure apparatus it is essential, that the anal sphincter muscle is not in a state of continuous opening or dilation by the transanally positioned shaft component of the device.

The normal sphincter tone is between 65 mbar and 120 mbar. Although the pressure exerted by such sphincter tone is not completely transformed into a corresponding balloon pressure, since the force of the sphincter muscle is only exerted along a length of approximately 3 to 6 cm of the anus channel, and therefore, the normal sphincter tone affects the shaft tube only in a localized area, both effects are not identical, but somehow comparable. As a consequence, it is assumed to be sufficient if a complete radial collapse or a complete radial infolding or invagination of the shaft wall takes place at least at a radial pressure of the normal sphincter tone between 65 mbar and 120 mbar, or, correspondingly, if a substantial radial collapse (with a reduction to a residual cross-section of the drainage lumen of less than 50% of the initial cross-section of the drainage lumen in the completely unfolded, but pressureless state of the balloon) or a complete radial collapse or a complete radial infolding or invagination of the shaft wall takes place at least at a balloon filling pressure of 55 mbar or more, or if a complete radial collapse or a complete radial infolding or invagination of the shaft wall takes place at least at a balloon filling pressure of 65 mbar or more.

The elastic deforming and/or restraightening properties of the balloon carrying shaft tube envelope shall be adjusted so that, when the balloon is freely unfolded outside the body to a balloon filling pressure of 120 mbar or more, the cross-section of the remaining drainage lumen within the shaft tube is reduced with regard to the initial cross-section in the freely unfolded, but pressureless state of the balloon, by at least 10%, preferably by at least 25%, especially by at least 50%, in particular by at least 80%.

Furthermore, the balloon pressure-induced reduction of the cross-section of the drainage lumen within the shaft tube takes place either gradually, that is like a continuous, narrowing or collapsing, or abruptly, that is like a toggling between an open condition and a constricted condition, especially an infolded or invaginated condition.

The invention recommends that the elastic deforming and/or restraightening properties of the balloon carrying shaft tube envelope are adjusted so that, when the balloon is freely unfolded outside the body and pressurized to a balloon filling pressure of up to 5 mbar, the cross-section of the remaining drainage lumen within the shaft tube is reduced with regard to the initial cross-section in the freely unfolded, but pressureless state, by no more than 70%, that is to a residual cross-section of at least 30% of its freely unfolded initial cross-section in pressureless state.

Another preferred design rule is that the elastic deforming and/or restraightening properties of the balloon carrying shaft tube envelope are adjusted so that, when the balloon is freely unfolded outside the body and pressurized to a balloon filling pressure of up to 10 mbar, the cross-section of the remaining drainage lumen within the shaft tube is reduced with regard to the initial cross-section in the freely unfolded, but pressureless state, by no more than 90%, that is to a residual cross-section of at least 10% of its freely unfolded initial cross-section in pressureless state.

On the other hand, the elastic deforming and/or restraightening properties of the balloon carrying shaft tube envelope may adjusted so that, when the balloon is freely unfolded outside the body and pressurized to a balloon filling pressure of up to 25 mbar, the cross-section of the remaining drainage lumen within the shaft tube is reduced with regard to the initial cross-section in the freely unfolded, but pressureless state, to a residual cross-section of no more than 50% of its freely unfolded initial cross-section in pressureless state.

A further preferred embodiment is characterized by the fact that the elastic deforming and/or restraightening properties of the balloon carrying shaft tube envelope are adjusted so that, when the balloon is freely unfolded outside the body and pressurized to a balloon filling pressure of up to 45 mbar, the cross-section of the remaining drainage lumen within the shaft tube is reduced with regard to the initial cross-section in the freely unfolded, but pressureless state, to a residual cross-section of no more than 20% of its freely unfolded initial cross-section in pressureless state.

It is within the scope of the invention that the envelope of the balloon carrying shaft segment of the device, when positioned inside the patient in transanal position, radially flattens, collapses, infolds or invaginates at a normal sphincter tone, and gradually returns to its preformed cross-section when the tone of the anal sphincter is lowering and the anal canal begins to open up, whereby the force that is elastically erecting the shaft tube envelope is larger than the force that is resting on the outside of the shaft tube, which is exerted by the filling pressure of the filling medium acting inside the balloon.

In contrast to the transanal sealing devices described in the prior art for patients with chronic fecal incontinence, where in many cases the anal structures already show degenerative changes and the anal canal often presents as very inconsistent in length and diameter, intestinal tubes of the design according to the invention are used primarily in patients with normal anorectal anatomy. This usually normal anatomy eliminates the need for a counter-rolling movement of the terminal balloon portions from both sides axially toward the anus, as a functional feature for spontaneously adapting the balloon body to anatomy that can vary greatly from one individual to the next. A special inversion of the balloon ends during the mounting of the balloon on the shaft body is therefore unnecessary. The tapered transanal segment of the balloon body should preferably have a length of 2 to 5 cm, preferably 2.5 to 3.5 cm, to be able to accommodate the anal canal in its full, anatomically normal linear extent.

In case of an embodiment of the device according to the invention, equipped with a preformed, mushroom shaped balloon, the transanal segment extends into a proximal, pre-anal balloon formation, which in the freely unfolded stated has a constant or equivalent diameter as the transanally positioned portion of the balloon, whereby the balloon is extending beyond the anal rim by 2 to 5 cm, preferably 2 to 3 cm.

Alternatively, in a less preferable version of the mushroom-shaped balloon, the trans-anal balloon segment can be given an axial length, matching with the outer anal opening, the so called anal rim.

In all embodiments of the invented device, regardless of the preformed balloon shape, the segment of the shaft tube envelope, that is housed in by the balloon, is performing the above described elastic radial collapse, infolding or invagination and self-erection mechanics. This specific radial deformation is optionally combined with an elastic axial kinking or buckling and axial self-erection of the shaft wall envelope.

However, in addition to the preferred techniques described according to the invention for preventing irritation or perforation of the bowel wall by means of suitable balloon shaft arrangements, the features according to the invention can also be combined with the design principles of a counter-rolling movement of the terminal balloon enlargements or axially sealing action of the balloon from both sides. Here again, the invention ensures that the free distal end of the shaft is not pushed or deflected into the bowel in a traumatizing manner.

Currently, the preferred modality for the long-term care of fecally incontinent patients for periods of up to several days and weeks is so-called stool drains, a technology referred to as "indwelling stool drainage." The drainage catheters used for this purpose are usually placed in the patient's rectum by means of a balloon-like anchoring element or are secured against unintentionally slipping through the anus by the fact that the anchor balloon rests with suitable areal contact on the rectal floor.

In most of the drainage catheters that have been placed on the market, the balloon element securing the device in the rectum is disposed directly on a tube element that drains the stool through the anus. The stool is collected by a usually replaceable collection container attached to the proximal end of the drainage tube.

To ensure that the placement of the intracorporeal drainage segment is as atraumatic as possible, the portion of the drainage tube that is disposed in the rectum and the anus is preferably made of a soft material that is able to fold up or collapse under externally applied forces. The anal canal thus is not distended for long periods by the drainage tube, so damage to the anal structures is largely averted even with long periods of use. The technical implementation of such drains that are left in the body for up to several weeks is usually elaborate, and the associated cost thus largely rules out the use of so-called "indwelling drainage" for shorter periods of time.

In addition to stool drains for long-term placement, so-called fecal collectors are also currently used to care for incontinent immobile patients. In contrast to stool drains, these basically consist of a film bag that directly receives the stool. Fecal collectors are affixed directly to the perianal skin by means of adhesive surfaces provided on the bag. When used for several days, fecal collectors are often associated with injury to the perianal epidermis, due, on the one hand, to irritation caused by their adhesive attachment, and, on the other hand, to the continuously macerating effect of stool on the exposed skin. In addition, the collecting bags can detach and cause soiling. Due to the sometimes severe perianal irritation that is routinely observed, fecal collectors are normally used for only short periods of time.

The conceptually simplest form of transanal drainage of stool is represented by the so-called intestinal tube. This consists of a relatively short tube element, provided at the end away from the patient, i.e. the proximal end, with a funnel-like connector for connection to a draining and collecting containment system. The main problem with intestinal tubes is secure anal or perianal fixation of the device, to prevent the tube from sliding out of the anus and keep it from penetrating uncontrolledly into the rectum. The risk of traumatic penetration of rectal and higher portions of the bowel by the tip of the usually relatively stiff-walled shaft of the intestinal tube is a basic given and causes many users to completely refrain from the use of intestinal tubes.

To ensure better fixability, conventional intestinal tubes are, among other things, equipped with a balloon element, which is usually mounted at the distal, intrarectally placed end of the device. Embodiments having two separate balloons are also in use, the intrarectal balloon being supplemented by a preanal balloon located in front of the anus. The two balloons, which are mounted separately on the shaft body, are filled via a common supply conduit, and in the filled state have accommodated the anus between them, thereby largely securing the intestinal tube in position and largely preventing perforation. Nevertheless, when expanded tightly under pressure, the balloon elements caused local irritation of the structures with which they were in contact. Mechanically induced lesions were also found in the region of the anal canal, caused by the hard shaft of the tube resting directly against the tissue. Intestinal tubes equipped with double balloons in the design available at that time were therefore found to be unsuitable for long-term atraumatic placement in the rectum.

The present invention describes an advanced, combined anorectal access technique, primarily designed for a dynamic, self-adjusting, trans-anal seal performance, spontaneously following the actual tone and opening of the anal sphincter apparatus.

The invention is further designed for a continuous, irritation-minimizing, atraumatic long-term use, for patients with spontaneous or treatment associated liquid stools.

For this purpose, a catheter shaft body having special axial and radial buckling or folding properties is equipped with an approximately dumbbell shaped or mushroom shaped balloon element, which is mounted in a special manner distally on the shaft body and which is preformed to the required working dimension during the production of the balloon and thus requires no forceful expansion of its balloon envelope in order to reach its complete, functional shape serving to anchor the catheter transanally and to provide a transanal seal.

In the preferred application of the device on the patient, the fully preformed balloon is filled with a gaseous filling medium, as e.g. air, inside the patient only partially, to a flaccid state, whereby the flaccid envelope of the balloon body is shaping tensionless to the individual anorectal anatomy, thereby exerting the least possible transmural force on the balloon exposed tissues and structures, performing synchronously, in a close approximation to the actual, physiologically acting intra-rectal pressure. The flaccid balloon segment inside the patient's rectum takes up the rectally acting actual force and presses the transanal balloon segment against the mucosa of the anal canal, thus effecting a specific, self-adjusting seal performance.

The trans-anal balloon segment is preformed in manufacturing to a diameter, granting a radially directed, preferably multiple infolding or invagination of the residually dimensioned balloon envelope inside the anal canal. Such reserve folds allow for a tensionless adjustment of the balloon envelope to the present diameter or opening of the anal canal.

The aimed-for atraumatic effect of the device according to the invention is made possible in the context of the invention preferably by a combination of the particular elastic deforming and straightening properties of the shaft component supporting the balloon and a particular shaping of the balloon and positioning and fixing of the balloon components on the supporting shaft.

The invention is distinguished, in this regard, by a multi-step buffering of a deflection of the shaft.

by means of a tolerance range with simple, relative play between the catheter shaft and the balloon, i.e., with a minimal restoring force $F_r \approx 0$, in the presence of a deflection x from the neutral, force-free state by a value up to a first limit value $G_1$:

$$x \leq G_1 => F_r = 0 \pm \varepsilon,$$

where $|\varepsilon| \leq 10$ g, preferably $|\varepsilon| \leq 5$ g, particularly $|\varepsilon| \leq 2$ g.

In addition, beyond this tolerance range there is a restoring force due to deformation of the intrarectal balloon section, i.e., with a restoring force $F_r$ of the balloon envelope, in the presence of a deflection x from the neutral, force-free state by a value between a first limit value $G_1$ and a second limit value $G_2 > G_1$:

$$G_1 \leq x \leq G_2 => F_r \approx c_H \cdot (x - G_1),$$

where $c_H$ represents the spring constant of the balloon envelope inflated without pressure. This spring characteristic is determined not only by the material properties of the envelope, but also by the preformed geometry of the balloon envelope.

Above a second limit value, there is a restoring force due to deformation (e.g. axial kinking or buckling) of the catheter shaft, i.e., with a restoring force $F_r$ of the catheter shaft, in the presence of a deflection x from the neutral, force-state state by a value between above [sic] the second limit value $G_2$:

$$G_2 \leq x => F_r = c_K \cdot (x - G_2),$$

where $c_K$ is the (smallest) spring constant of the catheter shaft. Should the catheter shaft have various cross-sectional geometries, for example with predefined weak points, the region to be applied here is the one with the lowest spring constant $c_K$, since it is the first region to yield.

To eliminate the possibility that the wall of the rectum or the sigmoid colon adjoining the rectum will be perforated by the catheter shaft supporting the balloon, the catheter shaft is provided with the ability, in response to forced accidental deflections of the shaft body toward the bowel beyond the longitudinal axis of the shaft, to transition to an elastically buckled state in the form of one or more axial kinks or folds before the tip of the shaft can have potentially damaging effects on the bowel wall, and by the buckling of the shaft to absorb a further deflection of the shaft axis toward the bowel in such fashion that the force exerted on the tip of the shaft or any portions of the bowel wall in contact therewith can be kept largely constant. When the force operating on the shaft axis from a proximal direction is removed, the elastically acting shaft body spontaneously returns to its initial open-lumen, fully longitudinally straightened state.

In addition to this elastic buckling of the shaft body in response to a drastic, large deflection of the shaft, the invention describes specific positionings of the waisted balloon element on the shaft body supporting the balloon that absorb small deflections of the shaft inside the transanally placed balloon in an atraumatic, buffering manner and keep the stool-draining shaft lumen largely open, within the scope of the thus-permitted relative axial play between the shaft body and the balloon, or prevent kinking of the shaft body due to moderate deflections of the shaft.

To guard against sharp-edged kinks brought about by the folding or buckling of the shaft tube and potentially having a traumatic effect on adjacent tissue, the present invention describes a softly deformable sheath disposed on the surface of the shaft tube, preferably in fixed connection thereto, which surrounds the kinkable or foldable drainage tube over its entire length or at least spans the inside of the balloon (distance between the fixation points of the balloon on the shaft body). In addition to its protective effect, the sheath can also have an inherent elastic effect that can advantageously modify the elastic deformability properties and straightening properties of the shaft body for the respective specific embodiments of the device.

To optimize the anchoring and sealing function and the tissue compatibility of the described drainage device, the invention proposes the use of particularly thin-walled balloon envelopes, consisting of single or multiple layered materials having a preferably low volume expandability. The balloon bodies are shaped or preformed to their working dimension during production. The filling of the balloon element takes place in situ, preferably with a volume that is smaller than the volume of the balloon disposed on the shaft when unfolded freely and without pressurization outside the body. This eliminates the possibility of expansion of the balloon envelope. With such incomplete filling, the force acting in the balloon merely corresponds to the cumulative effect of the intrarectal pressure, the force imposed by the transanal sphincter and the force exerted by the buttocks on the preanal portion of the balloon envelope. In the ideal use case, both the rectal anchoring and the transanal sealing of the device become functionally effective as a result of the mere physiological intra-abdominal pressure acting on the balloon. This represents the least possible exertion of force by the balloon on the tissues with which it is in contact.

In the context of the invention, the waisted balloon providing a transanal sealing effect and dislocation-proof anchoring of the catheter shaft in the anal canal is fixed in a particular manner on the shaft body supporting the balloon. The shaft ends of the balloon are brought into relation with the distal, free end of the shaft body in a particular manner as a result of which the distal end of the shaft body positions itself in a specific way relative to the distal radius of the intrarectal balloon segment.

In the various inventively described embodiments of the relative arrangement of the balloon and the shaft, a major concern in each case is to prevent uncontrolled deflection of the distal end of the shaft out of the intrarectal balloon portion and toward the bowel, with the attendant risk of perforation.

The invention describes not only balloon shaft arrangements in which the balloon shaft ends are offset toward each other, resulting in an axial counter-rolling movement of the terminal balloon enlargements, but also balloon shaft arrangements with little or no such offset of the balloon shaft ends, in the latter case with a positioning of the kind that would be assumed spontaneously by the balloon ends when the balloon is unfolded freely and without stress on the shaft.

Different degrees of axially oriented deflection of the shaft body inside the balloon element are described in connection with the balloon-and-shaft arrangement according to the invention. Consideration is given both to slight, free relative movements between the shaft and the balloon and to other deflections of the shaft body that go beyond the free relative play of the two components and are absorbed by elastic deformation of the distal portions of the balloon envelope. Should the shaft move a longer distance toward the bowel beyond this deflection point, or should the entire balloon-supporting portion of the drain be dislocated from its transanal placement on into the bowel, the special design of the shaft body and its specific elastic deformability properties and straightening properties will prevent perforation of portions of the bowel by the fact that the shaft body supporting the balloon transitions to the state of axial kinking or buckling. If, for example in the event of dislocation of the catheter, the forward portions of the drain should forcibly collide with portions of the bowel wall, the elastically folding shaft body buckles away over its longitudinal axis in the form of one or more kinks, and thus absorbs the particular deflection of the shaft in a largely force-neutralizing manner. With the preferred use of polyurethanes as the base material for the shaft body, the buckling or kinking develops in such a way that after overcoming an initial force acting on the shaft body from an axial direction, the shaft immediately kinks sharply and the rest of the process of distance-shortening buckling can then take place with much less axial force exerted on the tip of the shaft.

When the particular force, which is acting on the shaft is released, the shaft body spontaneously straightens out gradually back to its open-lumen, original longitudinal shape.

The elastic shaft body behaves in a similar manner when a gross movement or position change of the patient's body causes a single axial kink in the shaft, in the sense of an angling of the transanal segment relative to the intrarectal segment of the shaft body. Here again, the elastic shaft body preferably kinks by an appropriate angle even under low force, and spontaneously realigns itself in its longitudinal axis when the body returns to its normal position.

In addition to the described atraumatically acting buckling or kinking over the longitudinal axis of the shaft, the shaft is also similarly designed so that the shaft body folds in on itself radially under low force in a manner that is tolerated by the tissue. Thus, even under the normal tone exerted by the anal sphincter muscle, the shaft body is provided to fold substantially radially in on itself or collapse to a smaller-sized diameter. When the sphincter muscle tone relaxes, the folded-in shaft body is provided to straighten out again to its original diametral dimension or spontaneously open into the particular released anal canal.

This radial foldability makes it possible, in cases of long-term placement of the shaft body in the anus, to avoid a permanent widening (dilation) of the anal structures of the kind that can be expected with a rigid, non-collapsible tube body.

For the drainage of liquid stools, internal diameters of the shaft tube of approximately 12 to 20 mm are performing sufficient, diameters of 15 to 18 mm are preferred.

The shaft tube preferably consists of elastically acting polyurethanes (PUR) of Shore hardnesses 60A to 95A and preferably has wall thicknesses of approximately 0.2 mm (with an internal diameter of 12 mm) to approximately 0.5 mm (with an internal diameter of 22 mm).

In dimensioning the wall thickness and choosing the material hardness (Shore hardness) of the shaft tube, in the cited internal diameter range of 12 to 22 mm, it should further be kept in mind that the portion of the shaft tube supporting the balloon must have sufficient self-straightening ability to counteract the balloon filling pressure bearing against the outside of the shaft, and thus to prevent a lumen-narrowing or -occluding collapse of the drainage lumen. With the balloon unfolding freely outside the body, under filling pressures of up to approximately 45 mbar the drainage lumen of the shaft tube should preferably be reduced, in the region of its greatest narrowing, to no more than 20% of its freely unfolded initial dimension, and at 25 mbar to no more than 50%.

To further increase the lumen-preserving, elastic residual stress of the shaft tube, the latter can also be suitably modified in individual sections, such as, preferably, the transanal segment, by an increase or variation in wall thickness, an increase or variation in material hardness, a shaping or molding of the wall of the balloon carrying shaft segment to a corrugated profile, or by a segmental change in the nature of the material.

In addition to polyurethanes, the following may also be contemplated as shaft materials: silicones, SEBS, rubber, PUR/PVC blends, PUR/PVC co-extrusions, PVC, or PUR/Polyamide co-extrusions.

The protective sheath of the shaft tube can also be formed and applied as a single, continuous cylindrical element, but it can also, in further embodiments of the device, be implemented as a dumbbell- or hourglass-shaped element or have disk- or spherical enlargements at its distal and proximal ends. The sheathing body, besides being implemented as a continuous element, can alternatively consist of a plurality of individual unconnected or spaced-apart segments.

The sheath is preferably fashioned of foam material having elastically deformable, self-straightening properties, for example of the kind known from polyurethane foams. The self-straightening action of the foam jacket can supportively contribute to the automatic opening of a folded or deformed tube lumen, and also, where appropriate, to the axial untwisting thereof. The wall thickness of the draining shaft tube, which is then continuously and fixedly connected to the surrounding foam jacket, can optionally be reduced by implementing the shaft and the jacket as a composite of materials. It may be possible by this means to improve the elastic properties of the tube body and to optimize the overall tissue-friendliness of the drainage tube in the folded or deformed state. By a calibrated combination of the elasticity of the tube body and its restoring force upon folding or kinking with the elastic restoring effect of the overlying foam jacket, the material composite can be given an optimally low overall lumen-straightening elasticity while at the same time providing the best possible protection for the adjacent tissue.

In addition to being implemented as an elastically, viscoelastically or even non-elastically acting foam body, the sheath can also be implemented as an elastically or non-elastically acting body that is disposed electively fixedly or non-fixedly on the shaft body and is in the form of a gel body or absorbent-cotton-like body, or a particularly soft solid body of low Shore hardness made from materials such as, for example, silicone, polyurethane or SEBS. The preferred Shore hardnesses of such bodies range from approximately 10A to 70A, but preferably from 20A to 50A.

With respect to foam-based sheaths, Shore hardnesses in the range of 30A to 90A, but preferably 40 to 70A, are considered particularly advantageous. The corresponding wall thicknesses of the foam sheath range from preferably approximately 1.5 mm to 4.0 m, particularly advantageously from 2.0 to 3.0 mm.

The elastic self-straightening properties of the sheath of the shaft tube can further be used to give the so-equipped composite shaft body the necessary resistance to balloon filling pressures bearing externally on the shaft, which pressures, if sufficiently high, can lead to lumen-narrowing partial collapse of the draining tube lumen.

The invention further describes particular arrangements or structural combinations of the distal, bowelward end of the sheath relative to the portions of the balloon envelope that form the forward, frontal radius of the intrarectal balloon segment and relative to the forward, distal end of the shaft tube supporting the sheath.

Described below, in the context of specific exemplary embodiments, is the elastic folding and straightening behavior of a foam-reinforced drainage tube and a drainage tube without sheathing in response to force imposed axially and radially on the shaft.

BRIEF DESCRIPTION OF THE DRAWINGS

Further features, characteristics, advantages and effects will become apparent from the following description of a few preferred embodiments of the invention and by reference to the accompanying drawing.

DETAILED DESCRIPTION OF THE PREFERRED EMBODIMENTS

Figure 1A:
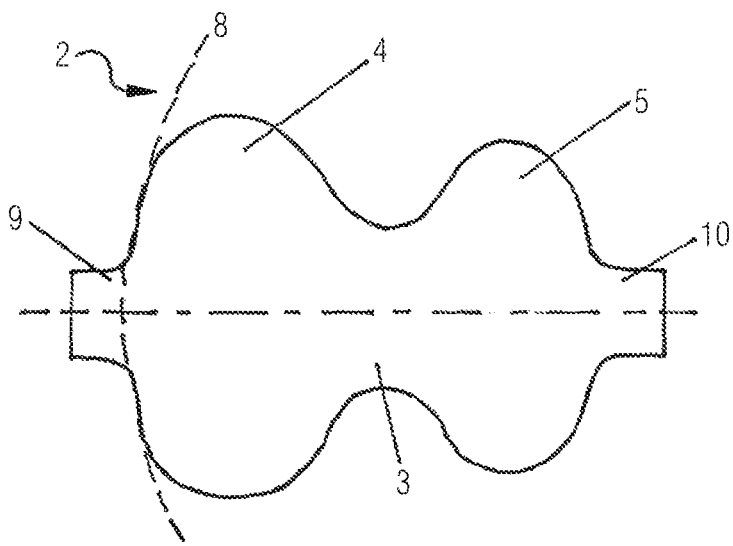
FIGS. 1a to 1c show, schematically and by way of example, a waisted balloon envelope, tapered in its middle section to an hourglass or dumbbell shape, unfolded spatially freely and without pressurization.
Figure 1B:
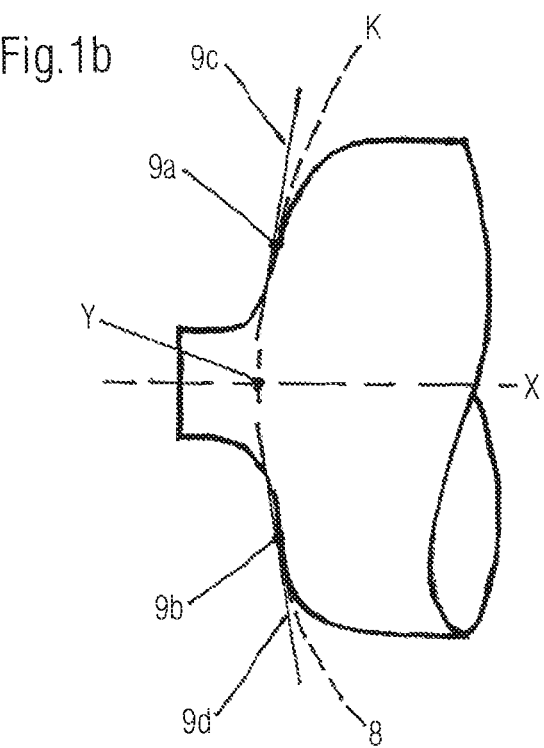
Figure 1C:
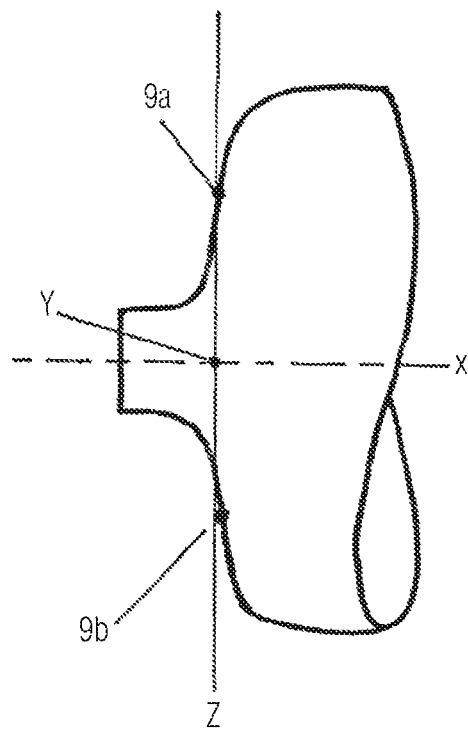

FIG. 1 shows a longitudinal section through a freely unfolded balloon body 2 that has already been shaped to its functional working dimension during production, with its free balloon shaft ends 9 and 10. The forward balloon radius 8 of the intrarectal balloon segment, facing frontally toward the bowel lumen, is indicated as a broken line.

The frontal balloon radius 8 is constructed from the two inflection points 9a and 9b and the two tangents 9c and 9d respectively belonging to these points. On this basis, a circle is constructed that intersects the two inflection points 9a and 9b and whose tangents (9c, 9d) in these points correspond to those of the inflection points. The apex Y is derived from the intersection point of the circumference of the circle with the axis X of symmetry of the balloon.

In the following description of the frontal apex of the intrarectal balloon enlargement, the intersection point of the line Z connecting the two inflection points to the axis X of symmetry will be used to simplify the representation of the point on the balloon envelope that ranges the farthest distally.

The balloon body comprises two spherical or approximately spherical enlargements, one at each end, the distal, intrarectal balloon enlargement 4 being connected via a middle, diametrally tapered or waisted segment 3 to the proximal, preanal enlargement 5. The middle, waisted segment 3 is placed in the anal canal and accordingly takes on the structures of the anus between the terminal balloon enlargements. The middle taper of the balloon ensures, on the one hand, the largely dislocation-proof positioning of the drainage device in the anal canal under the pulling and pushing forces that are exerted axially on the device under typical use conditions, and, on the other hand, permits particularly large-area and therefore efficient sealing of the balloon envelope with respect to the wall or mucosa of the anal canal. The middle segment also serves a protective function, in that continual direct mechanical contact of the structures of the tube shaft with the sensitive tissues of the anal canal is prevented by the protectively acting envelope of the waisted intermediate segment. To achieve good sealing performance, the wall thickness of the balloon envelope in the transanal segment should be approximately 10 to 50 µm, but preferably only 10 to 20 µm. The diameter in the transanal segment 3 should be approximately 15 to 45 mm, preferably 20 to 30 mm. Due to the relatively large diameter of the transanal balloon envelope, radially inwardly directed invaginations of the balloon envelope form as it is placed transanally. The radial invagination of the residual balloon envelope in this section eliminates the need for forceful expansion of the envelope wall to seal the anal canal between the catheter shaft and the wall of the anal canal.

Complete preforming of the waisted balloon body to the functional working dimension during the production of the balloon eliminates the need for the expansion, under high, non-physiological pressure, of the usually volume-expandable, non-preformed or only partially preformed balloon envelope used with intestinal tubes having conventional anchor balloon elements, and, in contrast hereto, permits balloon filling pressures that are always experienced as low and that have little or no adverse effect on tissue perfusion in the tissues adjacent the balloon.

The balloon component is preferably made from a very thin-walled, only slightly volume-expandable and overall dimensionally stable material with little tendency toward herniation, which material, although exhibiting the properties of a physiologically compatible soft film in the preferred wall thickness range of a few micrometers, nevertheless does not deform uncontrolledly with increasing filling pressure, and also limits that tendency of the balloon to slip in response to tension exerted on the catheter shaft from the outside which must be expected with highly volume-expandable materials, such as, for example, natural rubber or silicone, and thus enables the drainage device to provide a good transanal anchoring effect that is markedly superior to that of volume-expandable materials. Micro thin-walled balloon films made of, for example, polyurethanes with Shore hardnesses of 70A to 95A, preferably 85A to 90A, provide an envelope stability as called for by the invention. The wall thickness of the balloon envelope in the region of its terminal enlargements should be approximately 7 to 45 µm, preferably 10 to 20 µm.

Suitably thin-walled balloon films are preferably formed using materials of little or no volume-expandability, such as, for example, polyurethane (PUR), for example of the specification Pellethane 236380A or 90A, Dow Chemical Corp., or alternatively Elastollan of grades 1180A to 1195A, BASF AG. Alternatively, PVC or blends of PUR and PVC, coextruded PUR/PVC materials, coextruded PUR/Polyamide materials, coextruded PUR/Pebax materials, Pebax, or Polyethylenes, allowing for elastic deformation properties comparable to or even lower than those of polyurethane can be used.

Such thin-walled balloon films formed into complex shape can preferably be produced by hot molding from previously extruded raw tubing material, a method that gives the formed balloon films unusual strength due to the polymer orientation that can be obtained in this way. Balloon films according to the invention can also be formed directly from the extruded, still soft, amorphous tube molding compound (in-line molding).

Dipping processes and corresponding production from liquid PVC or PUR materials may also be contemplated. The welding together of single layers of film to form balloon bodies is also conceivable.

The filling of the balloon is preferably effected with a filling volume calculated to be less than the volume of the balloon with the balloon envelope mounted on the shaft and unfolded without pressurization. Such incomplete filling ensures that, once filled, the balloon envelope will not progress immediately to the state of being fully expanded on all sides, thus attaining filling pressure values in excess of the intrarectally and transanally acting physiological forces. In the state of incomplete filling of the balloon envelope, the sum of the forces acting intrarectally, transanally and pre-anally on the balloon have the effect of a force acting transmurally and uniformly on all sides on the tissue exposed to the balloon. Proper partial filling is preferably ensured by the use of a filling syringe provided with suitable volume markings and supplied with the product.

Figure 2:
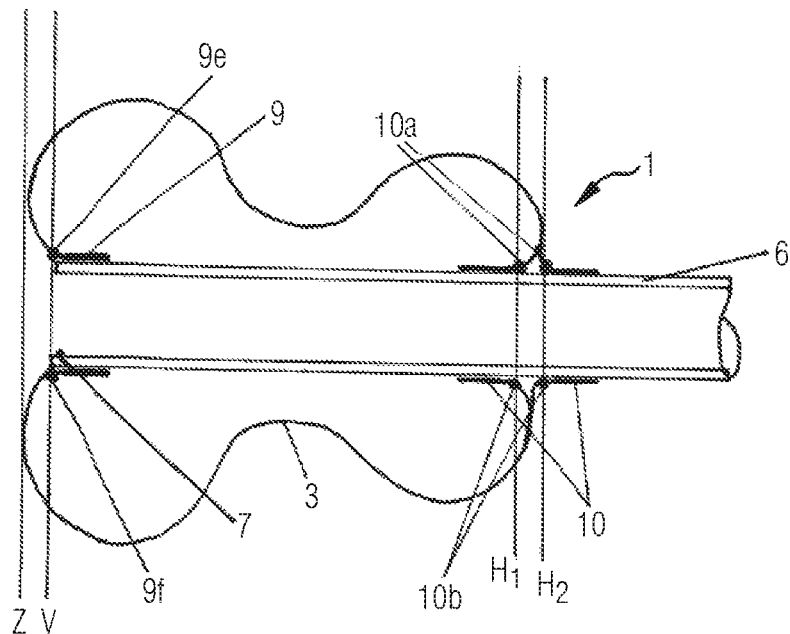
FIG. 2 shows an embodiment of the device in which the distal end of the shaft tube, directed toward the bowel, is connected nearly flushly to the distal shaft end of the balloon, and when the balloon envelope is unfolded freely and without pressurization, terminates nearly flush with the frontal radius of the intrarectal segment of the balloon.

FIG. 2 shows a longitudinal section through an intestinal tube 1 according to the invention, comprising an hourglass- or dumbbell-shaped balloon element 2 mounted at the distal end of a shaft tube 6. The balloon element has spherical- or discoid enlargements at its ends. Disposed in the middle region between the enlargements is a tapered, for example cylindrically or approximately cylindrically shaped waist-like segment 3. In this embodiment, the distal balloon shaft end 9 is mounted on a shaft tube 6 in such a way that the transition points 9e and 9f where the bottom balloon radius passes over into the cylindrical portion of the balloon shaft terminate flush or nearly flush with the free distal end of the shaft tube 6. The connecting line V between points 9e and 9f will be referred to hereinafter as the forward fixation line and describes the particular mechanically acting fixation points of the distal balloon end on the shaft tube supporting the balloon. In the described embodiment, the free distal end of the shaft tube therefore lies on the forward fixation line V, which in turn is surpassed in a distal direction by the connecting line Z of the inflection points of the balloon shoulder radii, as a result of which the frontal, distally protruding portion of the intrarectal balloon envelope prevents the free end of the shaft from coming into direct contact with portions of the bowel and thus acts as a mechanical buffer.

In the described embodiment, the fixation of the proximal balloon shaft end 10 on the shaft tube is guided by the state of free unfolding of the balloon envelope, the distal balloon shaft first being connected. The proximal connection is made electively either at rear fixation line $H_1$ (with the balloon shaft end 10 inverted in a distal direction) or at rear fixation line $H_2$ (with the balloon shaft end extending outward in a proximal direction). The rear fixation lines are constructed analogously to the forward fixation lines, from the transitions 10a and 10b of the bottom balloon shoulder radii to the balloon shaft and their connecting line.

Figure 2A:
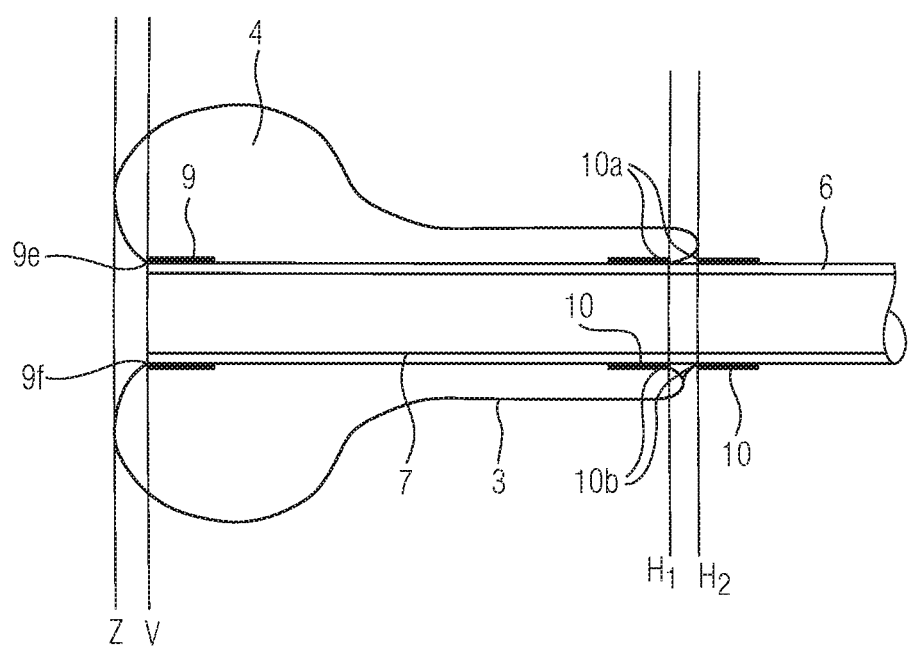
FIG. 2a shows a device with a mushroom-shaped balloon component, comprising an intrarectal segment and a transanal segment.

FIG. 2a shows a simplified embodiment of the device with a mushroom-shaped, preformed balloon, having only one distal, spherical or discoidal enlargement 4 for intrarectal positioning and retention of the device, which is proximally extended by a tapered balloon section 3a of relative thereto smaller diameter, preferably having the same diameter as the trans-anal balloon segment described in this disclosure, but having a length, which is matching with the outer opening of the anal canal, or in a preferred embodiment, exceeding the anal rim by 2 to 5 cm, so that the user can control the balloon filling inside the patient's bowel by visual inspection and/or tactile judgement.

Figure 2B:
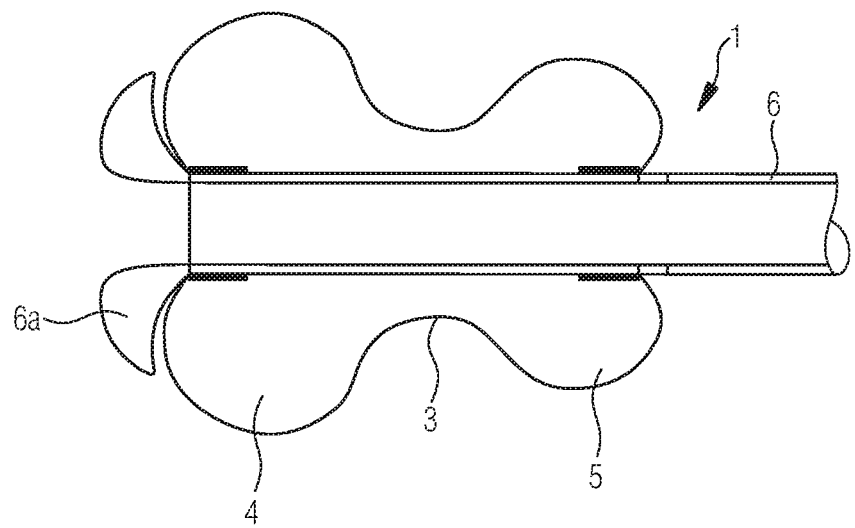
FIG. 2b shows a device as described in FIG. 2, whereby the distal end of the shaft tube is extended by a cone-shaped, insertion facilitating element, exceeding the distal radius of the intra-rectal balloon segment.

FIG. 2b shows another embodiment of a device according to the present invention, comprising a dumbbell- or mushroom-shaped balloon component, whereby the distal shaft end is extended by a component 6a with cone- or olive-shaped outer surface and an open lumen in the center, which projects beyond the distalmost part of the intrarectal balloon component 4 and is extending the distal balloon radius 8, thereby facilitating the insertion of the device through the anus into the rectum. The insertion aiding component 6a is preferably made from a soft, deformable, e.g. gel- or foam-based material. The frontal radius of component 6a laterally adjacent the tip of the component 6a is preferably large, reducing the likeliness of causing an irritation or a traumatic injury of the bowel wall. In case of a bowel-wards directed dislocation of the device from its regular trans-anal position, a potential bowel injury is prevented by the particular axial buckling performance of the shaft tube component, described as a main feature in the invention.

Figure 2C:
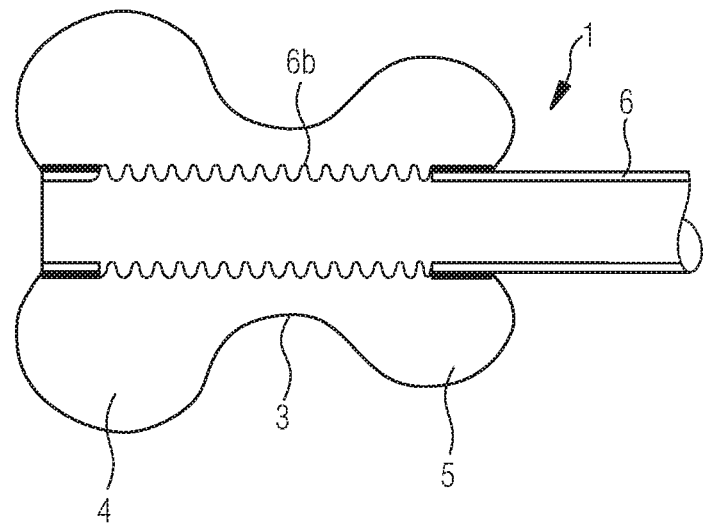
FIG. 2c shows a device as described in FIG. 2, whereby the envelope of the balloon carrying segment of the shaft component is molded to a corrugated profile.

FIG. 2c shows a modification of the device according to the present invention as described in FIG. 2, whereby the balloon carrying segment of the shaft component 6 is molded to a corrugated profile 6b. The corrugation of the shaft tube envelope allows for an axial bending of the device by 90 to 180 degrees, keeping the lumen of the tube largely opened and granting an unimpaired drainage performance of the flexed tube component. Compared to a non-profiled tube shaft component, the particular, corrugated profile 6b allows for a reduction of tube wall thickness, while at the same time enhancing the promptness of the elastic axial and radial deformation and erection of the tube.

The above described elastic bending and deformation properties of the corrugated profile 6b can be realized, for example, by making at least the regarding shaft element from Polyurethane (PUR), especially by use of a material with durometer of 85A, and/or by designing an inner diameter from 15 mm to 20 mm, especially of about 17 mm, and/or a tube wall thickness of 0.5 to 0.7 mm, and/or a corrugation amplitude of 2.5 to 3.0 mm, and/or a wavelength of the corrugation of 2.0 to 3.0 mm. In particular, by one or more of these design features, the appropriate shaft collapse at normal sphincter tone and the elastic erection of the shaft to its shaped profile, withstanding a certain balloon filling pressure, resting on the outside of the shaft tubing, can be achieved.

Such corrugation 6b can be molded into the tube profile, either over the entire length of the balloon carrying shaft tube segment or only in fragmented portions of it.

Figure 2D:
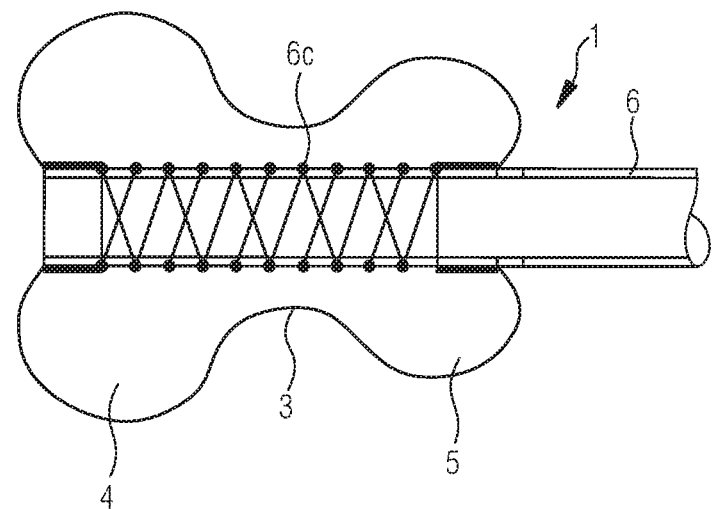
FIG. 2d shows the balloon carrying segment of the shaft component, supplemented by an additional mesh-like structure, modifying the elastic deformation and erection of the shaft tube.

FIG. 2d shows the balloon carrying segment of the shaft component 6, reinforced by an additional, lumen erecting, mesh-like structure 6c. Said mesh 6c can be made from elastic material, as e.g. Polyurethane (PUR). The mesh 6c is structurally connected to the stool draining tube layer, either by bonding or by extrusion or molding it onto or into the tube or shaft surface during an extrusion or molding process adjusted accordingly.

Figure 2E:
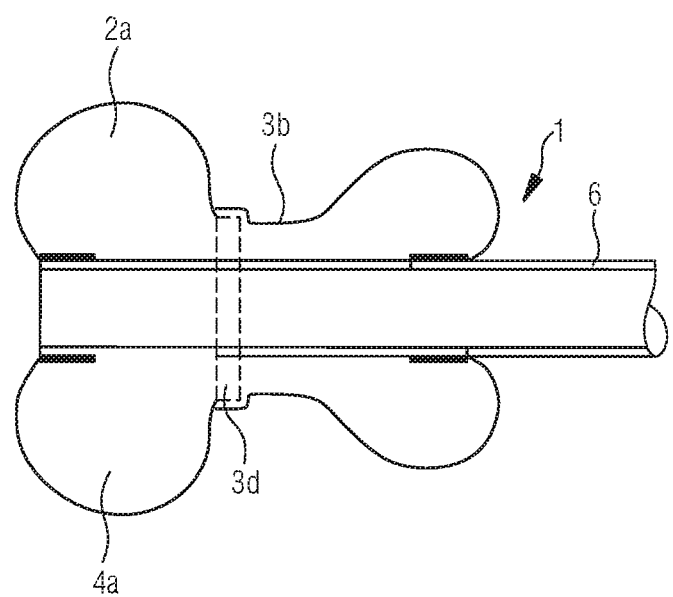
FIG. 2e shows a particular balloon design, whereby the dumbbell or mushroom shape of the balloon is assembled from two separate balloon segments, integrating a particularly thin-walled balloon envelope in the trans-anal segment of the assembled balloon, enhancing the seal performance of the balloon within the anal canal.

FIG. 2e shows a balloon design 2a, whereby the balloon is assembled from two or more separate balloon segments. The assembled balloon comprises a trans-anal segment 3a, that is having a particularly low wall thickness, allowing for an enhanced sealing performance of the balloon within the anal canal.

When molding the balloon components from pre-extruded PUR tubing in a standard hot-molding procedure, the balloon segments of lower diameter typically have a higher thickness than the balloon portions of a relatively larger diameter.

In the invented device, the sealing performance is enhanced by the continuous, tightly sealing contact of the tapered trans-anal balloon segment to the mucosa of the anal canal. Therefore, a minimized thickness of the trans-anal balloon segment is of advantage. In order to provide the herein required balloon shapes, the trans-anal segment is molded as a separate component and in a second step connected to the other enlarged sections.

Furthermore, different parts of the assembled balloon can be made of materials of different durometers, e.g. making the tapered, middle or proximal balloon segment from a higher durometer PUR material of Shore 55D to 65D and minimizing wall thickness to less than 10 μm, whereby the trans-anal section combines optimized sealing with enhanced shape stability, preventing a deformation of the dumbbell or mushroom shape at an increased balloon filling pressure. In contrast, the intra-rectal balloon section 4a of the assembled balloon 2a can be made of a material, that is of lesser compliance than the adjoining balloon section 3b, allowing for a more compliant balloon expansion at increased balloon filling pressure.

The separately molded segments are connected to each other, e.g. by an overlapping seam 3d, where the balloon ends are e.g. welded or bonded together tightly.

Figure 2F:
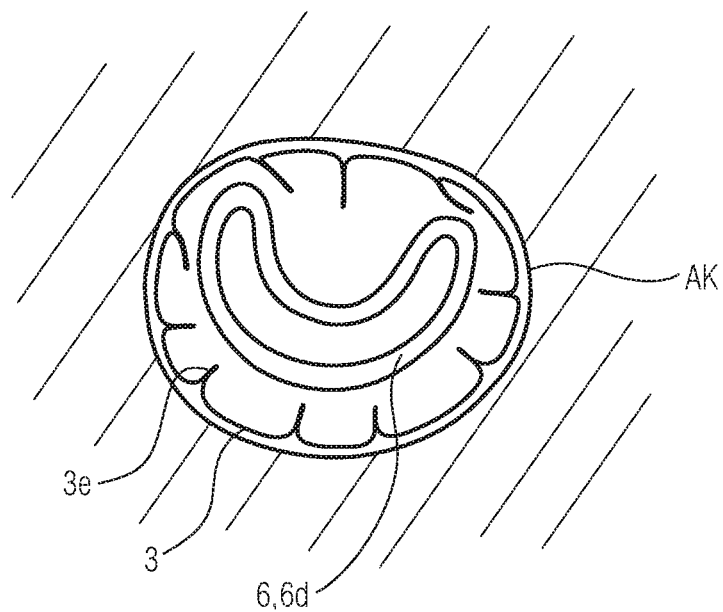
FIG. 2f shows the trans-anal segment of the device positioned inside the anal canal, consisting of two concentric tube-like structures, picturing the sealing performance of the outer balloon wall, and the stool draining function of the inner shaft tube.

FIG. 2f pictures the tapered, middle or proximal section of the balloon in situ, positioned inside the anal canal AK. The normal tone of the anal sphincter muscle causes the inner one of the two concentric balloon and/or tubing structures, namely the stool draining shaft tubing 6, to collapse from its preformed, preferably circular profile to an infolded profile 6d, preventing a permanent opening and dilation of the anal sphincter. At the same time, the outer structure, the trans-anal balloon segment 3, is kept in a seal effecting contact to the anal mucosa, whereby the force that is pressing the balloon film to the inner surface of the anal canal is taken up inside the rectum, following the actual rectal forces dynamically. The residual wall portions of the trans-anal balloon segment are invaginating into folds 3e, radially directed towards the center of the anal canal.

Once the anal tone is lowering and/or the anal canal is opening, the inner shaft tube erects and opens its lumen. Thereby, the self-erecting elastic force is exceeding the force exerted onto the shaft by the pressurized balloon filling. The shaft tube shall not collapse at balloon filling pressures of 25 mbar to more than 50% of its largest cross-section.

On the other hand, a balloon filling pressure of 50 mbar or more shall result in a substantial radial collapse, with a reduction to a residual cross-section of the drainage lumen of less than 80% of the initial cross-section of the drainage lumen in the completely unfolded, but pressureless state of the balloon.

A balloon filling pressure of 60 mbar or more shall result in a substantial radial collapse, with a reduction to a residual cross-section of the drainage lumen of less than 90% of the initial cross-section of the drainage lumen in the completely unfolded, but pressureless state of the balloon.

Finally, a balloon filling pressure of 65 mbar or more shall result in a substantial radial collapse, with a reduction to a residual cross-section of the drainage lumen of less than 95% of the initial cross-section of the drainage lumen in the completely unfolded, but pressureless state of the balloon.

Figure 3:
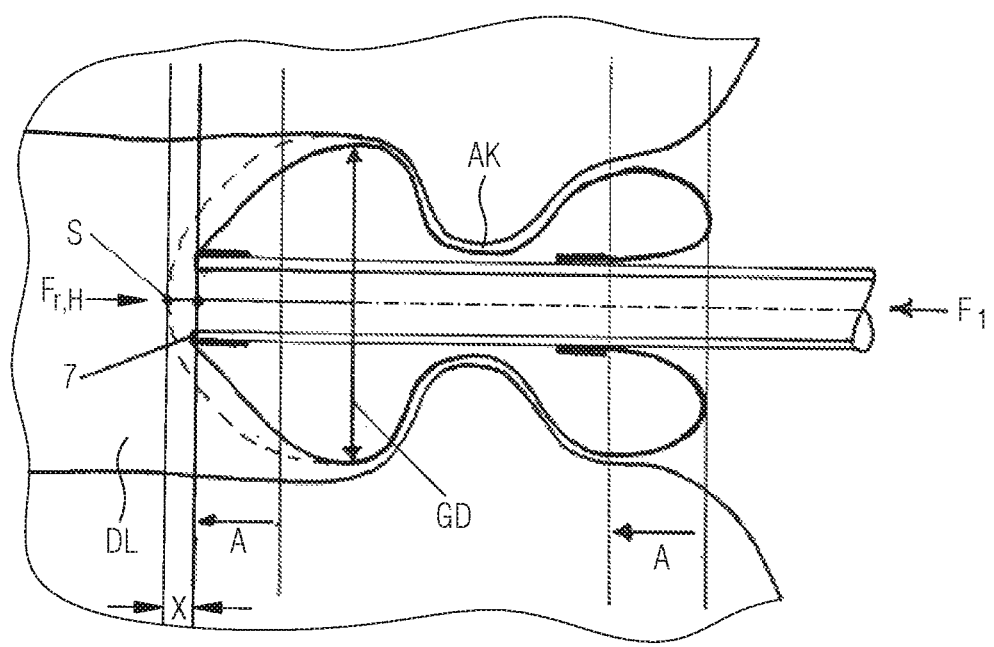
FIG. 3 shows the embodiment variant described in FIG. 2 with the device placed transanally, in the state of an axial deflection toward the bowel of the shaft tube inside the balloon body mounted on the shaft tube by an amount A, resulting in a corresponding elastic deformation of the forward envelope portions of the intrarectal balloon segment by amount A, thereby limiting the deflection of the shaft.

FIG. 3 shows the device described in FIG. 2 in transanal placement in the anal canal AK, in the state of axially oriented deflection into the intestinal lumen DL of the catheter shaft 6 inside the balloon mounted on the shaft tube, by an amount A in response to the force $F_1$ imposed on the shaft in the shaft longitudinal axis.

The advancement of the distal shaft tube end 7 into the intestinal lumen DL is limited by the elastic deformation of the frontal balloon wall portions of the intrarectal balloon segment 4, which deformation counteracts the free deflection of the shaft. In the implementation of the device and the acting force $F_1$ depicted here, the distal shaft tube end and thus the forward fixation line V do not pass into the intestinal lumen beyond a maximum deflection distance A predefined by the elastic deformation properties of the intrarectal balloon envelope and thus constituting a limit.

The proximal reference point for the determination of the deflection distance A is the rear fixation line H (H1 or alternatively H2) in the unloaded state in the absence of an imposed force $K_1$.

In the inventive shaping of, dimensioning of, and choice of material for the balloon envelope, the maximum possible deflection distance A of the distal end of the tube shaft should approximately correspond to the apex S of a radius constructed over the largest diameter GD of the intrarectal balloon enlargement 4. The largest diameter GD in this case refers to the respective diameter with the balloon in the freely unfolded, unpressurized state.

To ensure suitable limitation of the deformation of the balloon envelope directed relatively toward the bowel, the balloon body 2 is preferably made from a material of low elastic deformability, a choice that is especially important for the preferred thin-walled implementation of the balloon envelope in the low micrometer range; typically volume-expandable materials, such as, for example, natural rubber or silicone, are largely ruled out for the production of the balloon.

Figure 4:
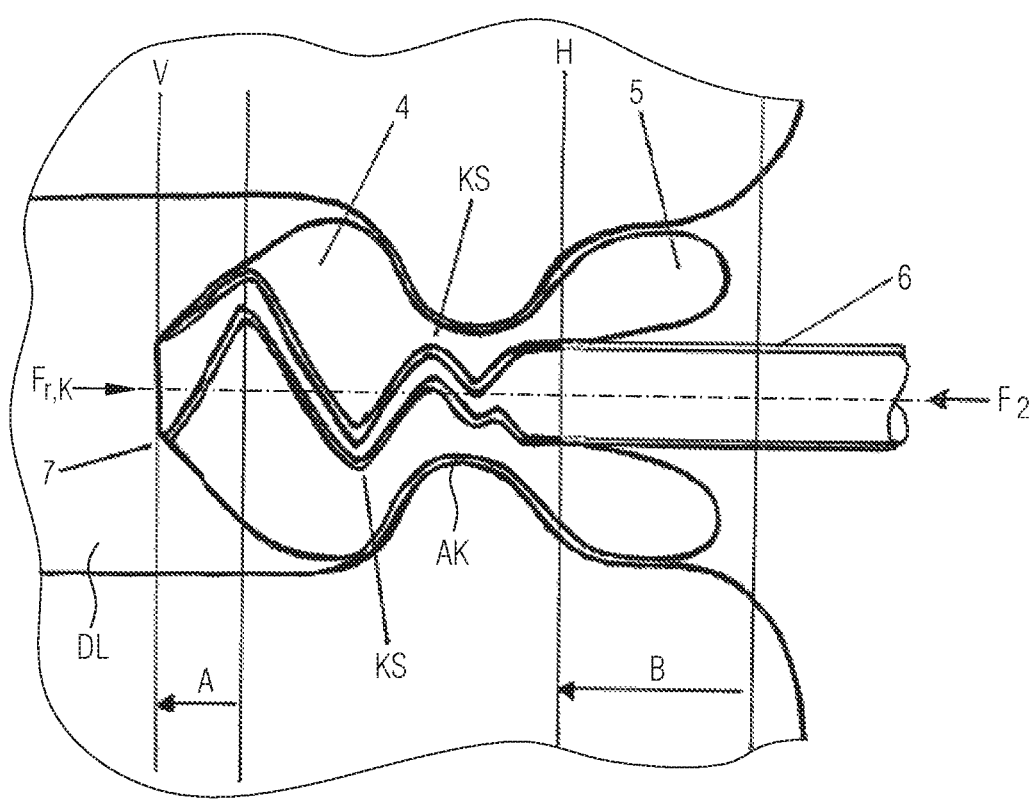
FIG. 4 shows the embodiment variants described in FIG. 2 or FIG. 3 with the device placed transanally, in the state of an axial deflection toward the bowel of the shaft tube inside the transanally placed balloon body mounted on the shaft tube by an amount B which cannot be absorbed by elastic deformation of the envelope portions of the intrarectal balloon segment to limit the deflection of the shaft, but instead gives way to single or multiple folding or kinking of the shaft tube over its longitudinal axis, whereas the forward envelope portions of the intrarectal balloon segment are deflected toward the bowel merely by the amount A.

FIG. 4 shows the device described in FIG. 2 and FIG. 3 in the state of an axial deflection of the catheter shaft toward the bowel inside a transanally placed balloon in the presence of a force $F_2$ acting on the catheter shaft from a proximal direction that exceeds the force $F_1$ described in FIG. 3.

When a certain critical force $F_{kink}$ is exceeded, single or even multiple axial kinking (KS) of the shaft tube 6 occurs. At the instant of the kinking or buckling of the shaft tube, the axially acting resistance of the shaft tube to the force $K_2$ acting on the shaft from a proximal direction abruptly gives way and the shaft tube deflects farther to as much as the full distance B, the force action exerted by the shaft tube on the frontal portions of the intrarectal balloon segment being nearly constant.

However, the maximum deflection of the forward fixation line V by amount A is not exceeded during the deflection of the shaft by amount B, a fact that is decisive for the inventive safe fixation of the free, potentially perforating shaft end 7.

The proximal reference point for determining the deflection distance B is, in turn, the rear fixation line H (H1 or alternatively H2) in the unloaded state in the absence of an imposed force K2.

In like manner, conversely, a force exerted on the shaft tube from distally to proximally initially results in a proximally directed deflection of the shaft body inside the transanally placed balloon and a corresponding deformation of the proximal balloon portions of the preanal balloon segment 5. With increasing force action and the excedence of a critical force, even in this deflection case the shaft tube 6 passes into the previously described buckled state KS and allows a further deflection of the shaft in a proximal direction under a then constant force acting on the shaft.

Such a kinking or buckling behavior of the device is relevant primarily when portions of the bowel are resting distally on the frontal portions of the balloon or when a forced deflection of the shaft tube into the bowel completely dislocates the device from its transanal fixation and the intrarectal portions of the device impinge on the bowel wall.

In the respective embodiments of the present invention, the critical force $K_{kink}$ should preferably be reached at a weight force imposed axially on the shaft of approximately 150 to 1000 grams, particularly preferably, however, at forces in the range of 200 to 500 grams.

Figure 5:
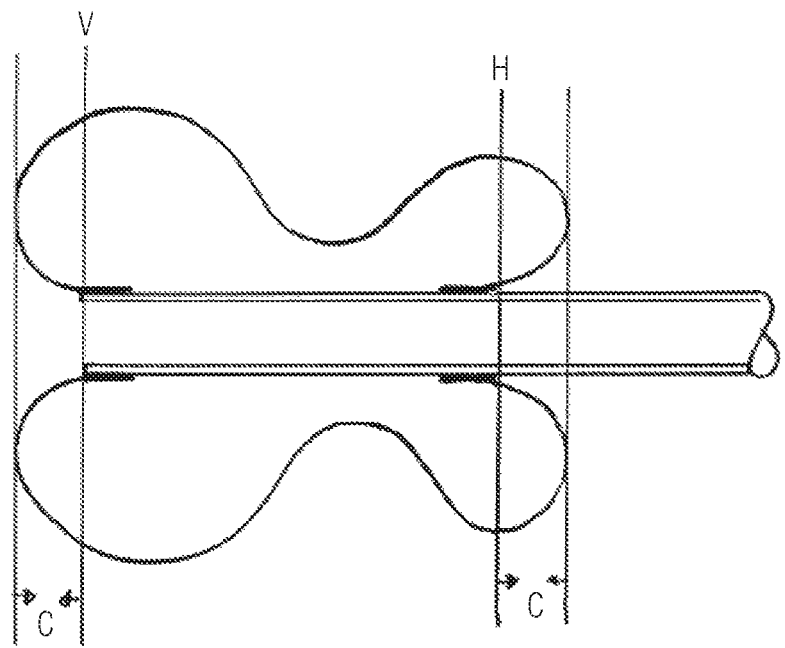
FIG. 5 shows another embodiment variant of the device in which, with the balloon body unfolded freely and without pressurization, the shaft ends of the balloon body are inverted on both sides by an amount C and in this position are fixed on the shaft tube.

As FIG. 5 shows, the invention also proposes, in addition to the specific consideration of larger deflections of the shaft tube inside the transanally placed balloon, embodiments in which the forward and rear fixation lines V and H of the balloon shaft ends are offset toward each other (inverted) on the shaft tube by a defined amount C, whereby smaller axial deflections of the catheter shaft for the distance C can be buffered by an axial relative movement between the balloon and the shaft without the occurrence of deformation of the envelope of the intrarectal balloon segment or distal displacement of the forward fixation line V beyond balloon radius 8. Farther-reaching deflections of the shaft that exceed the buffering distance C permitted by the inversion of the fixing ends are dampingly absorbed, in an analogous manner to the embodiment of FIG. 3, by elastic expansion of the envelope.

With a shaft outer diameter of approximately 12 mm, the inwardly directed offset VF of the fixation lines V and H should preferably be approximately 10 to 12 mm. With a shaft outer diameter measuring 15 mm, the offset VF should correspondingly be equal to 12 to 16 mm. The reference point for the offset is the respective connecting line Z between the inflection points of the radii where they transition to the balloon shoulders of the freely unfolded, unpressurized balloon.

Figure 6:
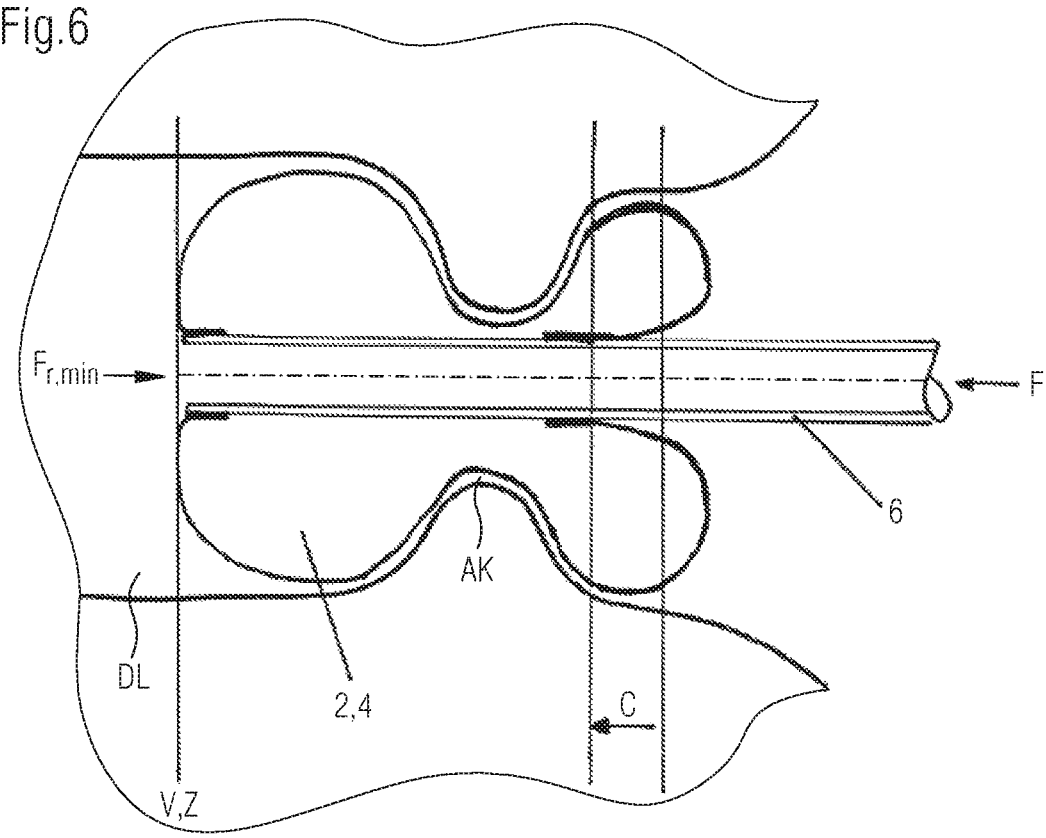
FIG. 6 shows the embodiment variant in FIG. 5 wherein the shaft tube is deflected axially toward the bowel inside the transanally placed balloon body mounted on the shaft tube by an amount C, under which circumstances the shaft allows itself to displace toward the bowel in free relative movement by an amount C, without the occurrence, described in FIG. 3, of the elastic deformation of the envelope portions of the intrarectal balloon segment to limit the movement of the shaft.

FIG. 6 shows the device described in FIG. 5 in the transanally placed state, in which the shaft tube supporting the balloon can be displaced toward the bowel inside the transanally placed balloon relatively freely by an amount C without accompanying elastic deformation of the envelope portions of the intrarectal balloon segment to limit the movement of the shaft.

Figure 7:
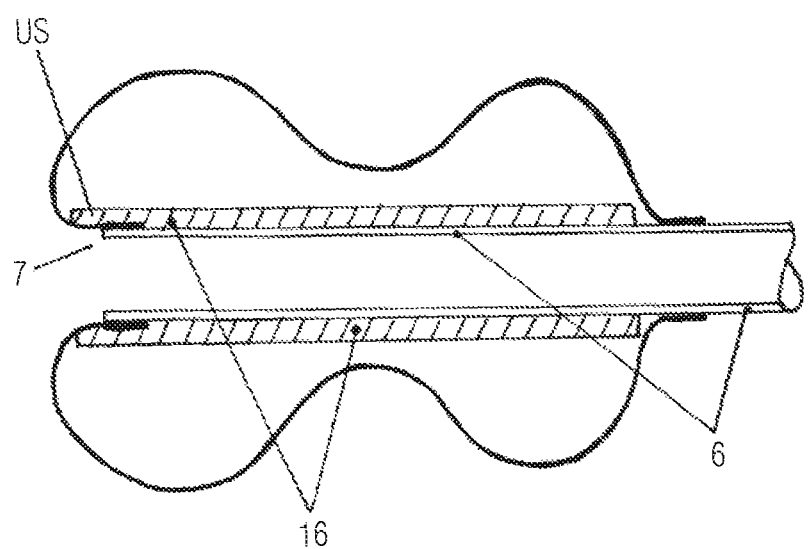
FIG. 7 shows in schematic cross section an embodiment of the device in which the shaft tube supporting the balloon is supplemented by a sheath having a protective and/or elastically lumen-straightening effect.

FIG. 7 represents particular embodiments of the device in which the shaft tube 6 supporting the balloon 2 is supplemented by a sheath 16 that is protective and/or has an elastically lumen-straightening effect. The figure shows a longitudinal section through an intestinal tube 1 having a continuous sheath that is disposed on the shaft element 6 and consists of preferably foam-like, elastically deformable and spontaneously self-straightening materials.

The sheath 16 preferably extends beyond the distal end of the shaft tube 6 (protrusion US) and thus provides additional buffering protection for the bowel wall against the free end 7 of the shaft tube. The foam bodies in this case protrude past the distal end of the shaft tube by preferably 3 to 12 mm, and particularly advantageously by 4 to 8 mm.

Optionally, the sheath 16 can also extend in a proximal direction to the shaft tube section adjacent the preanal shaft segment.

Figure 8:
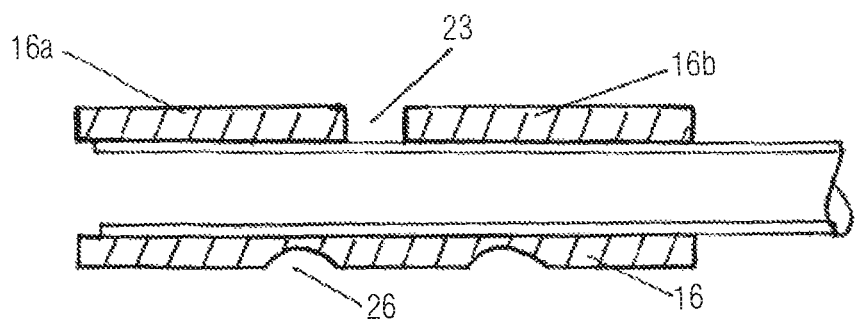
FIG. 8 shows in schematic cross section various embodiment variants of a shaft tube sheath corresponding to FIG. 7, with complete and partial segmentation of the jacket to predispose the shaft to kink or buckle axially.

According to FIG. 8, this embodiment of the device proposes a segmentation of the sheathing body 16. This is preferably effected inside the intrarectal balloon segment or, alternatively, in the transitional region between that segment and the transanal segment. The sheath body can be disposed on the drainage tube in the form of completely separate and spaced-apart units, e.g. 16a and 16b. Alternatively, a segmentation can be created by pronounced waisting 26 of a continuous jacket structure 16. The segmentation or waisting reduces the kinking stability of the shaft body in the intermediate segment region 23 or the region of the jacket taper 26, and thus preforms the axial kinking of the shaft in a desired shaft section (nominal kinking site). A plurality of such kinking sites can be arranged over the course of the sheathing of the drainage tube 6.

Given an internal diameter of the shaft tube of approximately 15 mm, the foam-free piece 23 between the foam elements 16a and 16b should preferably have a length of 5 to 15 mm, particularly preferably of 5 to 10 mm.

Figure 9:
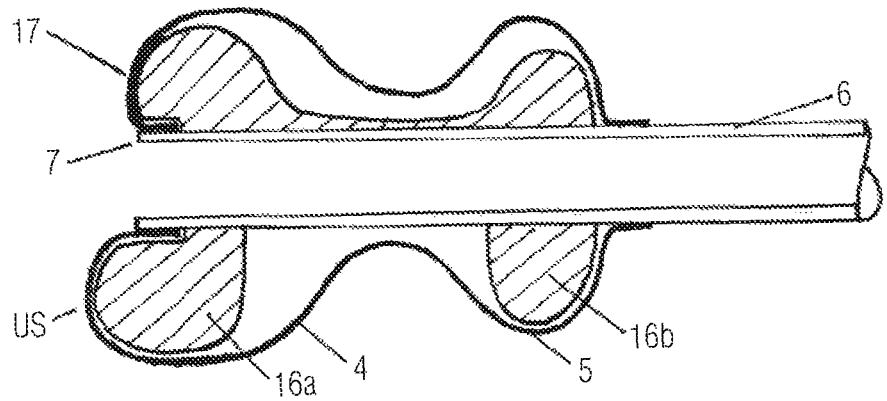
FIG. 9 shows further embodiment variants of a sheath.

According to FIG. 9, the distal foam segment 16a inside the balloon segment 4 can be configured to serve the function of an abutment component, for example in a ball or disk shape. The component provides an additional anchoring effect when the tube is inserted into the rectum. The abutment component thus prevents the tube from accidentally slipping out of the rectum before the balloon is filled. A foam segment 16b of corresponding shape, disposed on the shaft tube 6 inside the preanal segment 5, can serve as a guide mark for determining the correct insertion depth of the device in the anus.

A correspondingly shaped distal segment 16a can also have a buttressing effect on the shaft tube and limit the lateral tilting of the shaft toward the bowel wall. This effect is the more reliable, the farther distally toward the shaft opening 7 the abutment body is disposed on the shaft. The foam body preferably consists of a polyurethane foam, which, in turn, preferably has viscoelastic deformation and straightening properties.

The distal and proximal foam segments can also be continuously joined by a tapered intermediate segment, the foam body 16 thus forming a unit in the shape of an hourglass or dumbbell.

For improved protection against axial deflections of the distal end of the tube into the bowel, there can be a structural connection 17 of the distal balloon envelope to the distal-facing surface of the inwardly disposed foam body 16a or of the corresponding surface of the above-described dumbbell-shaped foam body, as the case may be. The connection 17 can be produced, for example, by areal gluing.

Analogously to the embodiment of FIG. 7, here again, the distal segment 16a or the distal end of the sheath 16 can extend beyond the distal free end 7 of the shaft tube by a defined projecting offset US.

Figure 10:
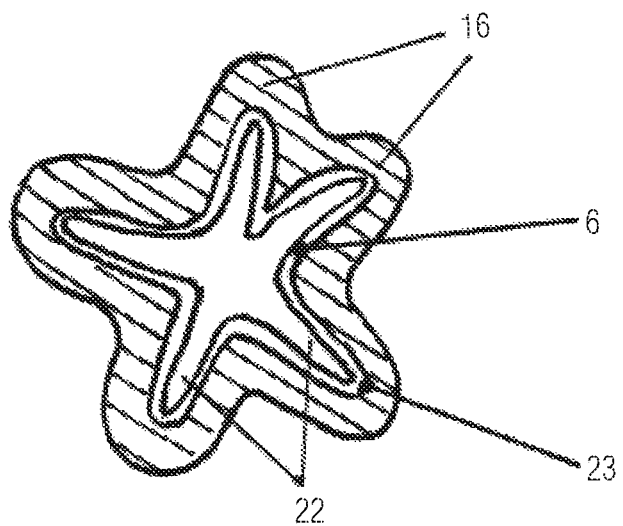
FIG. 10 is a cross section through the drain body showing the combined dampingly protective and elastically lumen-straightening effect of a sheath of the shaft tube in the presence of radial deformation or infolding of the shaft body.

FIG. 10 shows in cross section the radial invagination 22 of the wall of the shaft tube 6, and the corresponding folding of a foam jacket 16, which in this embodiment is mounted on the shaft tube in a continuously fixed manner. Potentially cutting edge formations 23 of the kind that can develop in the apex region of the invagination 22 are cushioned atraumatically softly in their effect on the adjacent tissue.

Preferably soft, elastically self-straightening polyurethane foams are used to fashion the shaft body. Analogously to the support lent to the axially acting elastic straightening of the deformed shaft tube wall, an elastically acting sheath supports the spontaneous radial straightening of a radially infolded shaft tube wall.

The foam elements can also be foamed directly onto the supporting tube during the production of the device, thus eliminating the need for areal connection to the supporting underlayer with solvents or glue.

Combinations of the following materials and properties, as examples, have proven advantageous for the material composite of the shaft body in all the presented embodiments of the device. The shaft tube 16 consists of a polyurethane of Shore hardness 70-90A and has an internal diameter of approximately 15 mm and a wall thickness of 0.2 to 0.3 mm. The foam jacket 16 has a wall thickness of approximately 1 to 5 mm, preferably 1.5 to 2.5 mm. Its consistency and elasticity correspond to those of the material MS SuperSoft 70P, from the company Filtrona Porus Technologies. This is an MDI-based hydrophilic PUR foam (MDI being a type of prepolymer).

The described combination permits an optimal straightening effect of the tube lumen and optimal protection of the adjacent body tissues.

Alternatively, it is possible to use softer foam sheaths whose elastic properties correspond, for example, to those of the material MS SuperSoft 60P.

Hard, less deformable foam sheaths can be produced, for example, from fiber-reinforced foams, such as, for example, MS 70P grade composite foam.

Figure 11:
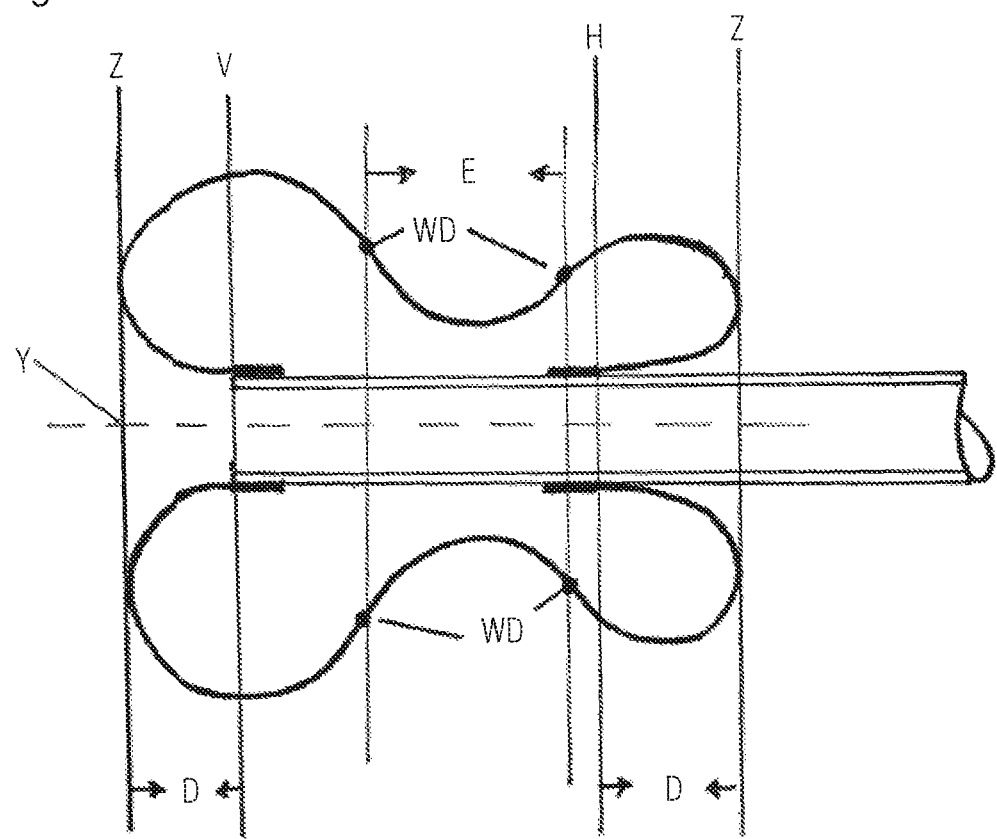
FIG. 11 shows a particular embodiment of the device for self-adjusting, axially oriented sealing of the balloon against the inner and outer openings of the anal canal, wherein the balloon shaft ends are inverted on the shaft tube on both sides by an amount D and are fixed on the shaft tube, thereby ensuring that the free, distal end of the shaft still assumes a position inside the intrarectal balloon segment even when the terminal balloon portions of the hourglass- or dumbbell-shaped balloon body maximally approach each other via an axial counter-rolling movement.

FIG. 11 describes a further option for the atraumatic securing of the distal end of the catheter shaft in drains having waisted balloon components according to the invention, in which the fixation lines V and H are offset toward each other in such a way that a pronounced counter-rolling movement of the terminal balloon segments occurs. The amount of the offset D of the fixation lines V and H on both sides should be, in total, smaller than/equal to the distance E between the inflection points WD of the shoulder radii of the distal balloon enlargement and WP of the proximal enlargement. The offset D is referred to the apices Z of the front and rear balloon radii, in similar fashion to its determination in the preceding figures.

The thus-enabled axial counter-rolling of the balloon enlargements 4 and 5 toward the external and internal anus are intended to permit dislocation-stable and well-sealing placement of the drain in the anus even in the presence of a shortened anal canal deviating from the norm. Here again, the free distal end 7 of the shaft tube is preferably connected congruently with the forward fixation line V of the distal balloon shaft end 9.

In the presence of a force acting axially on the shaft from a proximal direction, analogously to the embodiment of FIG. 3, given the inventive implementation of the balloon envelope and the shaft tube, the shaft tube end 7 remains limited in its maximal deflection inside the transanally placed balloon, such that a defined apex S is not surpassed by the free end of the shaft tube.

Figure 12:
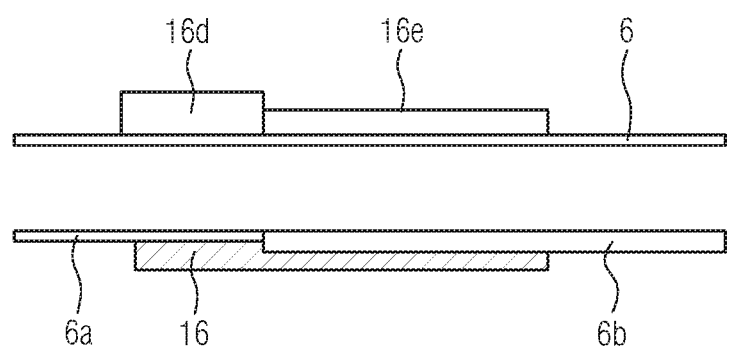
FIG. 12 shows further embodiments of the shaft body supporting the balloon.

FIG. 12 describes, in the lower half, an alternative embodiment of the components of the shaft body (shaft tube 6 and sheath 16) according to the invention, in which the design principle of axial buckling and radial folding of the shaft tube 6 can be realized from diverse elements by segmenting the shaft into sections 6a, 6b of materials having different hardnesses, wall thicknesses and deformation properties.

For example, the transanal segment of the shaft, or also the preanal or next proximally adjacent segment of the shaft, can, like the intrarectal segment of the shaft, be made of relatively hard, low-deformability material. The described buckling and folding effect can thus be limited to individual segments, while other segments are largely lumen-stable and counteract the reversible elastic deformation of the shaft.

In addition to the use of elastically deformable materials, it is also possible to contemplate the use of non-elastically, plastically acting shaft segments, made, for example, from PVC or PUR/PVC blends.

The filling of the proposed balloon elements preferably takes place through a filling conduit integrated into the wall of the shaft tube. A compressible, gaseous medium, such as air, is preferably used.

For volume-controlled filling, an injection element is preferably included with the device and specifies the particular filling volume by means of a suitable marking on the syringe body.

The filling of the balloon is preferably effected incompletely, with a filling volume corresponding to the volume accepted by the freely unfolded, unpressurized balloon mounted on the shaft, minus the corresponding volume accepted by the transanal balloon segment. The transanal balloon segment is defined in this context as the portion of the balloon between the inflection points WD and WP (see FIG. 11).

Particularly advantageous for attaining an optimally low filling pressure in conjunction with sufficient anchoring and sealing by the balloon is filling with a filling volume that corresponds to the previously determined filling volume, but increased by approximately 10 to 30 percent of the volume accepted by the transanal balloon segment.

The elastic folding and straightening behavior of a foam-sheathed shaft tube under axially and radially imposed force will be described further with reference to a specific exemplary embodiment.

Preferably, the shaft tube 6 is implemented as follows:

Elastollan 1180A (from the company BASF)

Internal diameter 15 mm

Wall thickness 0.3 mm

The shaft tube is connected to a dumbbell-shaped balloon 2, the latter being charged with variable filling pressures via a filling conduit. The foam sheath 16 is disposed continuously on the outer surface of the shaft tube inside the balloon and has a wall thickness of 2 mm. The foam material corresponds to the specification of type MS SuperSoft 70P, from the company Filtrona Porus Technologies.

The following table shows the maximum narrowing of the lumen of the shaft tube (the drainage lumen) that occurs in each case with a specific filling pressure imposed on all sides of the shaft body inside the balloon. The respective smallest transverse distance between the mutually approaching inner walls of the tube is taken as the drainage lumen dimension DM (especially its diameter) in the balloon-supporting section of the shaft.

The upper half of FIG. 12 shows a catheter shaft 6 with a sheath 16 consisting of two segments 16d, 16e, which sheath 16 is pushed onto the catheter shaft 6.

TABLE

Relationship between filling pressure and drainage lumen in a specific exemplary implementation of a foam-sheathed shaft tube

| Balloon filling pressure (mbar) | Drainage lumen dimension DM (mm) |
|---|---|
| 0 | 14 |
| 5 | 12-14 |
| 10 | 9-11 |
| 15 | 6-9 |
| 20 | 5-8 |
| 25 | 4-6 |
| 30 | 3-5 |
| 35 | 1-3 |
| 40 | 0-2 |
| 45 | 0 |

Table: Relationship between filling pressure and drainage lumen in a specific exemplary implementation of a foam-sheathed shaft tube The axial kinking of the shaft tube in response to a force $F_{kink}$ acting on the shaft somewhere along the shaft longitudinal axis occurs in this specific implementation of the device in response to a weight force of approximately 300 to 350 grams imposed in the region of the rear fixation line H.

The invention also proposes simple embodiments of the drainage device not provided with a sheath and having only a shaft tube as the balloon-supporting body.

The following table gives the deformation behavior of a shaft tube of equivalent design without a sheath.

TABLE

Relationship between filling pressure and drainage lumen with specific exemplary embodiments of a non-sheathed shaft tube

| Balloon filling pressure (mbar) | Drainage lumen dimension DM (mm) |
|---|---|
| 0 | 14 |
| 5 | 8-12 |
| 10 | 5-8 |
| 15 | 2-4 |
| 20 | 1-2 |
| 25 | 0 |

The axial kinking of the shaft tube in response to a force $F_{kink}$ acting on the shaft somewhere along the shaft longitudinal axis occurs in this specific implementation of the device in response to a weight force of approximately 200 to 250 grams imposed in the region of the rear fixation line H.

In addition to the transanal use of the device, intestinal tubes fashioned according to the invention can also be inserted and placed for perforation-safe placement in transabdominal, surgically created stomata/openings to the bowel or other natural body openings.

The described device can also be used, in the implementations proposed here, as a transanal inflow catheter or in the context of postoperative transanal tamponade following anal or rectal surgery. Particularly advantageous here have been found to be the transanal sealing function brought about by the middle, waisted balloon segment and the atraumatic positioning of the shaft tip even in the event of accidental, forced axial [word missing] of the shaft into the intestinal lumen, and the use of additional abutment bodies or foam bodies in the intrarectal and/or preanal enlargement of the balloon component.

The invention claimed is:

1. A device for the transanal drainage of stool from the rectum of a patient and/or for the transanal administration of inflowing fluid through a catheter-like element, comprising a catheter shaft and an inflatable balloon that is produced from a thin-walled soft film material of limited elastic deformability and is preformed during production to have at least two adjoining balloon sections, namely at least a distal radially enlarged balloon section having a larger tubular radius, as well as at least a proximal, radially tapered balloon section having a reduced tubular radius, such that the distal, radially enlarged balloon section is placed intrarectally and the proximal, radially tapered balloon section is placed transanally, so that the proximal, radially tapered balloon section extends into an anal canal of the patient, wherein both ends of the balloon taper and are fixed at an axial distance from each other on a surface of a jacket of the catheter shaft, and wherein the catheter shaft comprises (i) elastic deforming and (ii) restraightening or self-erecting properties, which are designed in such a way that in the presence of a normal sphincter muscle tone of the patient bearing at resting tone against the catheter shaft from the outside, the catheter shaft deforms radially in the form of a radial collapse, infolding or invagination of the jacket of the catheter shaft, and, upon relaxation of the tone of the sphincter muscle of the patient, spontaneously straightens elastically again and releases a drainage lumen within the catheter shaft.

2. The device as in claim 1, wherein the elastic deforming and/or restraightening properties of the balloon carrying catheter shaft are adjusted so that, when the balloon is freely unfolded outside the body of the patient to a balloon filling pressure of 120 mbar or more, the cross-section of the drainage lumen within the catheter shaft is reduced with regard to an initial cross-section in the freely unfolded, but pressureless state of the balloon, by at least 10%, or by at least 25%, or by at least 50%, or in particular by at least 80%.

3. The device as in claim 2, wherein the balloon pressure-induced reduction of the cross-section of the drainage lumen within the catheter shaft takes place either gradually, that is like a continuous, narrowing or collapsing, or abruptly, that is like a toggling between an open condition and a constricted condition, especially an infolded or invaginated condition.

4. The device as in claim 1, wherein the elastic deforming and/or restraightening properties of the balloon carrying catheter shaft are adjusted so that, when the balloon is freely unfolded outside the body of the patient and pressurized to a balloon filling pressure of up to 5 mbar, the cross-section of the drainage lumen within the catheter shaft is reduced with regard to an initial cross-section in the freely unfolded, but pressureless state of the balloon, by no more than 70%, that is to a residual cross-section of at least 30% of the initial cross-section in the freely unfolded, but pressureless state of the balloon.

5. The device as in claim 1, wherein the elastic deforming and/or restraightening properties of the balloon carrying catheter shaft are adjusted so that, when the balloon is freely unfolded outside the body of the patient and pressurized to a balloon filling pressure of up to 10 mbar, the cross-section of the drainage lumen within the catheter shaft is reduced with regard to an initial cross-section in the freely unfolded, but pressureless state of the balloon, by no more than 90%, that is to a residual cross-section of at least 10% of the initial cross-section in the freely unfolded, but pressureless state of the balloon.

6. The device as in claim 1, wherein the elastic deforming and/or restraightening properties of the balloon carrying catheter shaft are adjusted so that, when the balloon is freely unfolded outside the body of the patient and pressurized to a balloon filling pressure of up to 25 mbar, the cross-section of the drainage lumen within the catheter shaft is reduced with regard to an initial cross-section in the freely unfolded, but pressureless state of the balloon, to a residual cross-section of no more than 50% of the initial cross-section in the freely unfolded, but pressureless state of the balloon.

7. The device as in claim 1, wherein the elastic deforming and/or restraightening properties of the balloon carrying catheter shaft are adjusted so that, when the balloon is freely unfolded outside the body of the patient and pressurized to a balloon filling pressure of up to 45 mbar, the cross-section of the drainage lumen within the catheter shaft is reduced with regard to an initial cross-section in the freely unfolded, but pressureless state of the balloon, to a residual cross-section of no more than 20% of the initial cross-section in the freely unfolded, but pressureless state of the balloon.

8. The device as in claim 1, wherein the jacket of a balloon carrying segment of the catheter shaft, when positioned inside the anal canal of the patient in a transanal position, radially flattens, collapses, infolds or invaginates at a normal sphincter tone, and gradually returns to its preformed cross-section when the tone of the anal sphincter is lowering and the anal canal begins to open up, whereby a force that is elastically erecting the jacket of the catheter shaft is larger than a force that is resting on the outside of the catheter shaft, which is exerted by a filling pressure of a filling medium acting inside the balloon.

9. The device as in claim 1, wherein the distal, radially enlarged balloon section is configured to retain or anchor the device in the rectum of the patient.

10. The device as in claim 9, wherein the distal, radially enlarged balloon section comprises a mushroom shape for retaining or anchoring the device in the rectum of the patient, as well as with distally adjoining proximal, radially tapered balloon section for a positioning inside the anal canal.

11. The device as in claim 10, wherein the proximal, radially tapered balloon section is configured to be positioned in the patient so that the proximal, radially tapered balloon section either ends at the level of the outer anal opening, namely the anal rim, or so that the proximal, radially tapered balloon section extends extracorporeally beyond the anal rim by 2 to 5 cm or by 2 to 3 cm.

12. The device as in claim 9, wherein the balloon comprises a waisted shape which is formed by two terminal balloon sections with a larger tubular radius, wherein one terminal balloon section is the distal, radially enlarged balloon section intended for an intrarectal, while the other terminal balloon section is configured for an extracorporeal placement, and, disposed therebetween and tapered relative thereto, a middle balloon section that has a reduced tubular radius and is configured to be placed transanally.

13. The device as in claim 12, wherein the distal, radially enlarged terminal balloon section and the terminal balloon section intended for an extracorporeal placement have approximately the same longitudinal cross sections.

14. The device as in claim 1, wherein the balloon is assembled from two or more separate balloon segments.

15. The device as in claim 14, wherein the assembled balloon comprises a trans-anal segment with a particularly low wall thickness, allowing for an enhanced sealing performance of the balloon within the anal canal.

16. The device as in claim 1, wherein a distal end of the catheter shaft is extended by a component with a cone-shaped or olive-shaped outer surface and an open, central lumen, which projects beyond a distalmost part of the distal, radially enlarged balloon section and extends a radius of the distal, radially enlarged balloon section.

17. The device as in claim 1, wherein a balloon carrying segment of the catheter shaft is molded to a corrugated profile entirely or partially.

18. The device as in claim 17, wherein the corrugated profile is a ring-shaped or spiral-shaped corrugation.

19. The device as in claim 17, wherein the corrugated profile has a corrugation amplitude of 2.5 to 3.0 mm.

20. The device as in claim 17, wherein the corrugated profile has a wave-length of the corrugation of 2.0 to 3.0 mm.

21. The device as in claim 17, wherein the corrugated profile has an inner diameter from 15 mm to 20 mm, or has a tube wall thickness from 0.5 to 0.7 mm.

22. The device as in claim 17, wherein the corrugated profile is made from an elastically deformable and self-erecting material, or from Polyurethane.

23. The device as in claim 1, wherein the catheter shaft is reinforced by an additional, lumen erecting, mesh-like structure entirely or partially along a balloon carrying segment of the catheter shaft.

24. The device as in claim 23, wherein the mesh-like structure is bonded onto the catheter shaft, or is extruded with the catheter shaft, or is molded into the catheter shaft.

25. The device as in claim 23, wherein the mesh-like structure is made from an elastic material or from Polyurethane.

26. The device as in claim 1, wherein in the presence of a greater axial deflection of a proximal end of the catheter shaft supporting the balloon toward the bowel, the segment of the catheter shaft carrying the balloon transitions to a state of single or multiple axial buckling.

27. The device as in claim 26, wherein a deflection of a proximal end of the catheter shaft is buffered by several steps, namely by means of a tolerance range with simple, relative play between the catheter shaft and the balloon in the presence of a deflection x from the neutral, force-free state by a value up to a first limit value $G_1$, where a restoring force $F_r$ is neglectable:

$$x \leq G_1, => F_r = 0 + \varepsilon,$$

where $|\varepsilon| \leq 10$ g, and, beyond this tolerance range, there is a restoring force due to a deformation of the distal, radially enlarged balloon section, with a restoring force Fr of the balloon carrying catheter shaft, in the presence of a deflection x from the neutral, force-free state by a value between a first limit value $G_1$ and a second limit value $G_2 > G_1$:

$$G_1 \leq x \leq G_2, => F_r = c_H*(x - G_1),$$

where $c_H$ represents a spring constant of the balloon carrying catheter shaft inflated without pressure, and, in the presence of a deflection x from the neutral, force-free state by a value above the second limit value $G_2$, there is a restoring force $F_r$ due to a deformation of the catheter shaft, with a restoring force Fr of the catheter shaft, in the presence of a deflection x from the neutral, force-free state:

$$G_2 \leq X, => F_r = c_K*(X - G_2),$$

where $c_K$ is a smallest spring constant of the catheter shaft.

28. The device as in claim 1, wherein the jacket of the catheter shaft is softly deformable, preventing traumatic effects on adjacent tissue potentially caused by a folding or buckling of the catheter shaft, and/or providing an inherent elastic effect that can modify the elastic deforming and/or restraightening properties of the catheter shaft.

29. The device as in claim 28, wherein the jacket of the catheter shaft is in the form of foam or gel-based elements.

30. The device as in claim 28, wherein the jacket of the catheter shaft is a foam or gel-based element and the jacket of the catheter shaft extends beyond a distal end of the catheter shaft by at least 5 mm.

31. The device as in claim 28, wherein the jacket of the catheter shaft is segmented, and/or has at least one change in a cross-section and/or comprises at least one recess.

32. The device as in claim 28, wherein the jacket of the catheter shaft is completely or partially surrounded outwardly by the balloon.

33. The device as in claim 32, wherein the jacket of the catheter shaft is fixed on the outer surface of the catheter shaft and is facing towards the inner side of the balloon, or is facing towards the inner side of the distal, radially enlarged balloon section.

34. The device as in claim 1, characterized by a folding of the catheter shaft, or by a folding of the catheter shaft along predefined circumferential regions of the catheter shaft.

35. The device as in claim 34, wherein the circumferential regions of the catheter shaft are predefined by cross-sectional tapers or recesses.

36. The device as in claim 1, wherein the balloon is preformed to the working dimension of the balloon during production, so that the balloon can be filled to the working dimension without pressurization and therefore without an elastic expansion of the balloon carrying catheter shaft, especially by an incomplete filling with a volume that is smaller than the volume of the preformed balloon.

37. The device as in claim 36, wherein the balloon is filled with a filling medium inside the patient only partially, to a flaccid state, whereby during the flaccid state the balloon is shaping tensionless to an individual anorectal anatomy of the patient.

38. The device as in claim 37, wherein the distal, radially enlarged balloon section inside the patient's rectum takes up the rectally acting actual force and presses the proximal, radially tapered balloon section against the mucosa of the anal canal, thus effecting a specific, self-adjusting seal performance.

* * * * *